(12) United States Patent
Furuya et al.

(10) Patent No.: US 6,340,686 B1
(45) Date of Patent: Jan. 22, 2002

(54) THIENOPYRIMIDINE COMPOUNDS, THEIR PRODUCTION AND USE

(75) Inventors: Shuichi Furuya; Nobuhiro Suzuki; Nobuo Choh, all of Tsukuba; Yoshi Nara, Suita, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/571,215

(22) Filed: May 16, 2000

Related U.S. Application Data

(63) Continuation of application No. 09/530,495, filed as application No. PCT/JP00/01777 on Mar. 23, 2000.

(30) Foreign Application Priority Data

Mar. 24, 1999 (JP) .......................................... 11-079371
Jan. 25, 2000 (JP) .......................................... 12-018019

(51) Int. Cl.$^7$ ..................... A61K 31/519; C07D 495/06
(52) U.S. Cl. ........................................ 514/258; 544/278
(58) Field of Search ........................... 514/258; 544/278

(56) References Cited

FOREIGN PATENT DOCUMENTS

| WO | WO 95/28405 | 10/1995 |
| WO | WO 96/24597 | 8/1996 |

*Primary Examiner*—John M. Ford
(74) *Attorney, Agent, or Firm*—Mark Chao; Elaine M. Ramesh

(57) ABSTRACT

A compound of the formula:

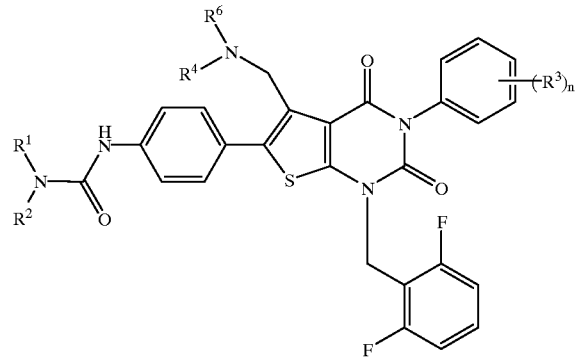

wherein $R^1$ and $R^2$ each is hydrogen, hydroxy, $C_{1-4}$ alkoxy, $C_{1-4}$ alkoxy-carbonyl or $C_{1-4}$ alkyl which may be substituted; $R^3$ is hydrogen, halogen, hydroxy or $C_{1-4}$ alkoxy which may be substituted; or adjacent two $R^3$ may form $C_{1-4}$ alkylenedioxy; $R^4$ is hydrogen or $C_{1-4}$ alkyl; $R^6$ is $C_{1-4}$ alkyl which may be substituted or a group of the formula:

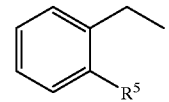

wherein $R^5$ is hydrogen or $R^4$ and $R^5$ may form heterocycle; and n is 0–5, or a salt thereof, has an excellent GnRH-antagonizing activity, and is useful for preventing or treating sex hormone-dependent diseases.

24 Claims, 1 Drawing Sheet

LH Concentrations in Castrated Cynomolgus Monkey Plasma

▲ control group 1    △ compound group 1
◆ control group 2    □ compound group 2
○ compound group 3

*% ratios respective reference values immediately prior to administration

THIENOPYRIMIDINE COMPOUNDS, THEIR PRODUCTION AND USE

This application is a continuation of copending application Ser. No. 09/530,495, filed Apr. 26, 2000.

TECHNICAL FIELD

The present invention relates to thieno[2,3-d]pyrimidine compounds exhibiting gonadotropin releasing hormone (GnRH) antagonizing activity, their production and use.

BACKGROUND ART

Secretion of anterior pituitary hormones undergoes feedback control by peripheral hormones secreted from target organs of the respective hormones and by secretion-regulating hormones from the hypothalamus, which is the upper central organ of the anterior lobe of the pituitary (hereinafter, these hormones are collectively called "hypothalamic hormones" in this specification). At the present stage for, hypothalamic hormones, the existence of nine kinds of hormones including, for example, thyrotropin releasing hormone (TRH), and gonadotropin releasing hormone [GnRH, sometimes called LH-RH (luteinizing hormone releasing hormone)] has been confirmed. These hypothalamic hormones are believed to show their actions via the receptors which are considered to exist in the anterior lobe of the pituitary, and efforts to find the receptor-gene expression specific to these hormones, including for humans, have been made. Accordingly, antagonists or agonists specifically and selectively acting on these receptors should control the action of the hypothalamic hormone and the secretion of anterior pituitary hormone. As a result, such antagonists or agonists are expected to be useful in preventing or treating anterior pituitary hormone diseases.

Known compounds possessing GnRH-antagonizing activity include GnRH-derived linear peptides (U.S. Pat. Nos. 5,140,009 and 5,171,835), a cyclic hexapeptide derivative (JP-A-61-191698), a bicyclic peptide derivative [Journal of Medicinal Chemistry, Vol. 36, pp. 3265–3273 (1993)], and so forth. Non-peptide compounds possessing GnRH-antagonizing activity include compounds described in WO 95/28405 (JP-A-8-295693), WO 97/14697 (JP-A-9-169767), WO 97/14682 (JP-A-9-169735) and WO 96/24597 (JP-A-9-169768), etc.

Peptide compounds pose a large number of problems to be resolved with respect to oral absorbability, dosage form, dose volume, drug stability, sustained action, metabolic stability etc. There is strong demand for an oral GnRH antagonist, especially one based on a non-peptide compound, that has excellent therapeutic effect on hormone-dependent cancers, e.g., prostatic cancer, endometriosis, precocious puberty etc., that does not show transient hypophysial-gonadotropic action (acute action) and that has excellent bioavailability.

DISCLOSURE OF INVENTION

Figure 1:
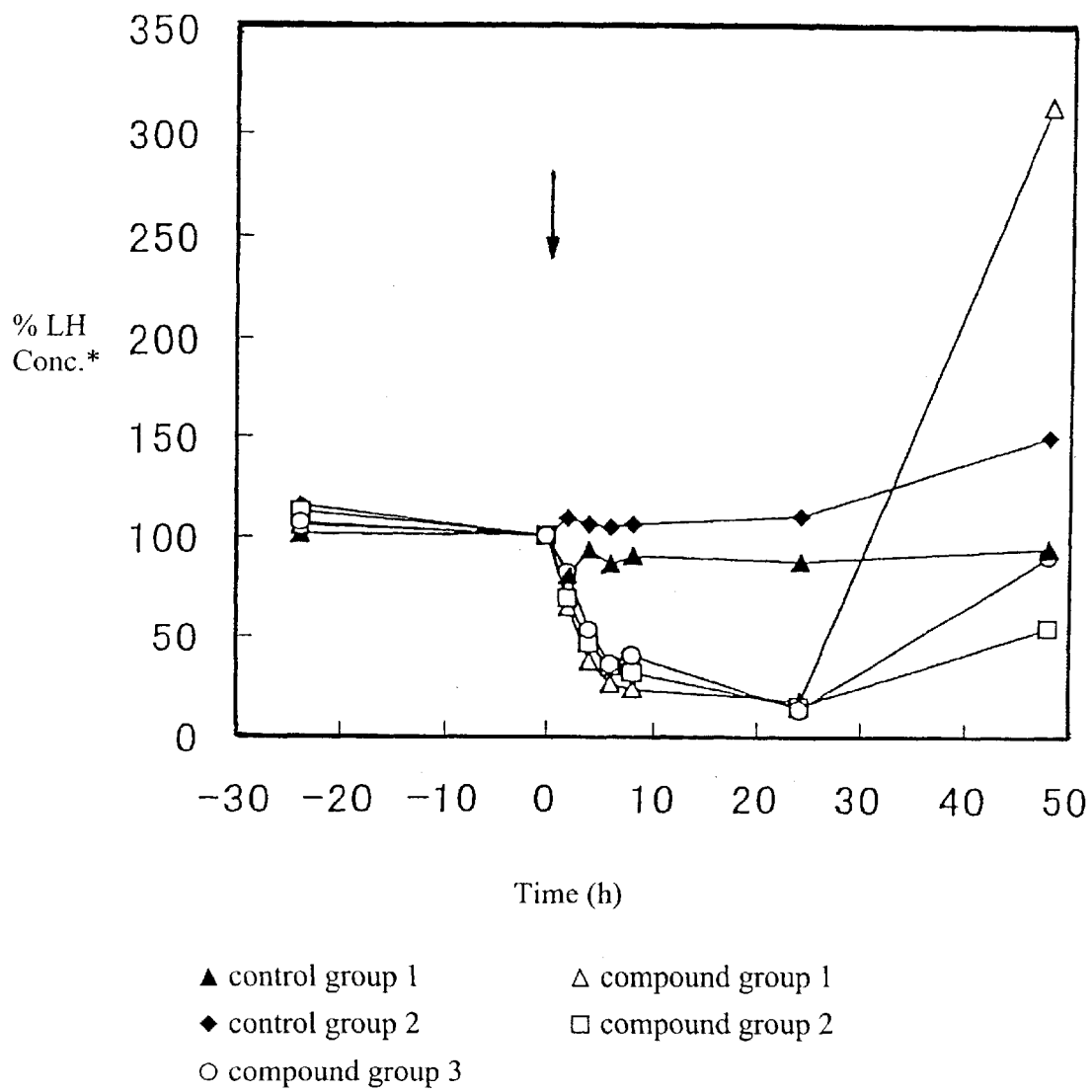
FIG. 1 shows the percent LH concentrations in test monkey plasma. In the figure, -▲- represents control group-1, -◆- represents control group-2, -△- represents compound group-1, -□- represents compound group-2 and -○- represents compound group-3, respectively.

We, the present inventors, have studied various compounds, and as a result, have found for the first time the following novel compound which has a substituent, a group of the formula: —NH—CO—NR$^1$R$^2$ wherein each symbol is as defined below, on the para-position of the phenyl group of the thieno[2,3-d]pyrimidine skeleton, or a salt thereof [hereinafter sometimes referred to briefly as compound (I)]. And we also have found out that compound (I) has an unexpected, excellent GnRH-antagonizing activity, based upon the above specific substituent, and low toxicity and is therefore satisfactory as a medicine having GnRH-antagonizing activity, and developed the present invention based on this finding.

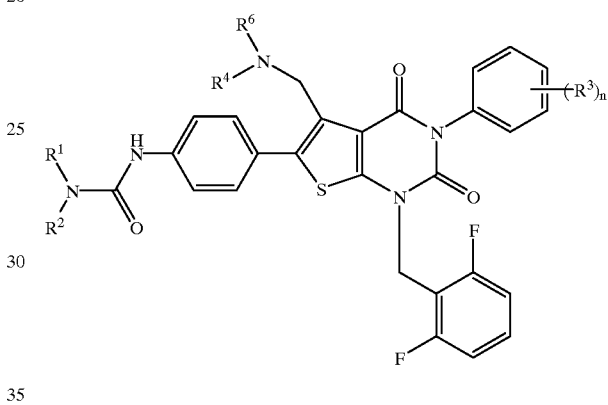

(I)

wherein

R$^1$ and R$^2$ each represents a hydrogen atom, a hydroxy group, a C$_{1-4}$ alkoxy group, a C$_{1-4}$ alkoxy-carbonyl group or a C$_{1-4}$ alkyl group which may be substituted;

R$^3$ represents a hydrogen atom, a halogen atom, a hydroxy group or a C$_{1-4}$ alkoxy group which may be substituted; or adjacent two R$^3$ may form, taken together, a C$_{1-4}$ alkylenedioxy group;

R$^4$ represents a hydrogen atom or a C$_{1-4}$ alkyl group;

R$^6$ represents a C$_{1-4}$ alkyl group which may be substituted or a group of the formula:

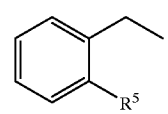

wherein R$^5$ represents a hydrogen atom or R$^4$ and R$^5$ may form, taken together, a heterocycle; and n represents an integer of 0 to 5.

Accordingly, the present invention relates to:

[1] a compound (I);

[2] a compound of the above [1] or a salt thereof, which is a compound of the formula:

(Ia)

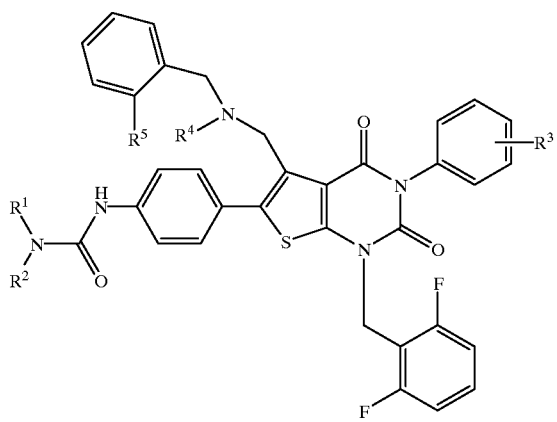

wherein R¹ and R² each is a hydrogen atom, a hydroxy group, a $C_{1-4}$ alkoxy group or a $C_{1-4}$ alkyl group which may be substituted; R³ is a hydrogen atom, a halogen atom or a $C_{1-4}$ alkoxy group; R⁴ is a $C_{1-4}$ alkyl group; and R⁵ is as defined above;

[3] a compound of the above [1] or a salt thereof, wherein R¹ is a $C_{1-3}$ alkoxy group;

[4] a compound of the above [3] or a salt thereof, wherein R² is a hydrogen atom;

[5] a compound of the above [1] or a salt thereof, wherein R³ is a hydrogen atom;

[6] a compound of the above [1] or a salt thereof, wherein R⁶ is a group of the formula:

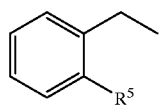

wherein R⁵ is as defined above;

[7] a compound of the above [2] or a salt thereof, wherein R⁴ is a $C_{1-3}$ alkyl group and R⁵ is a hydrogen atom;

[8] a compound of the above [1] or a salt thereof, wherein n is 1 or 2;

[9] a compound of the above [1] or a salt thereof, wherein R¹ is (i) a hydroxy group, (ii) a $C_{1-4}$ alkoxy group, or (iii) a $C_{1-4}$ alkyl group which may be substituted by hydroxy or $C_{1-4}$ alkyl-carbonyloxy; R² is a hydrogen atom, a $C_{1-4}$ alkyl group or a $C_{1-4}$ alkoxy-carbonyl group; R³ is a hydrogen atom, a halogen atom, a hydroxy group or a $C_{1-4}$ alkoxy-$C_{1-4}$ alkoxy group; or adjacent two R³ form, taken together, a $C_{1-3}$ alkylenedioxy group; R⁴ is a hydrogen atom or a $C_{1-3}$ alkyl group; R⁶ is a $C_{1-4}$ alkoxy-$C_{1-4}$ alkyl group or a group of the formula:

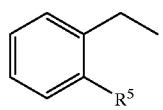

wherein R⁵ is a hydrogen atom or R⁴ and R⁵ form, taken together, a 5- or 6-membered heterocycle; and n is 1 or 2;

[10] a compound of the above [1] or a salt thereof, wherein R¹ is a hydroxy group, a methoxy group or a $C_{1-3}$ alkyl group; R² is a hydrogen atom or a $C_{1-3}$ alkyl group; R⁴ is a $C_{1-3}$ alkyl group; R⁶ is a benzyl group; and n is 0;

[11] 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione or a salt thereof;

[12] a process for producing a compound of Claim 1 or a salt thereof, which comprises reacting a compound of the formula:

(II)

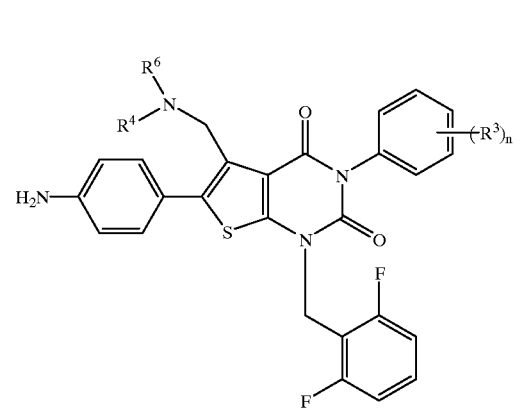

wherein each symbol is as defined above, or a salt thereof [hereinafter sometimes referred to briefly as compound (II)] with carbonyldiimidazole or phosgene, followed by reacting with a compound of the formula:

(III)

wherein each symbol is as defined above, or a salt thereof [hereinafter sometimes referred to briefly as compound (III)];

[13] a pharmaceutical composition which comprises a compound of the above [1] or a salt thereof;

[14] a pharmaceutical composition of the above [13] which is for antagonizing gonadotropin-releasing hormone;

[15] a pharmaceutical composition of the above [14] which is for preventing or treating a sex hormone dependent disease;

[16] a method for antagonizing gonadotropin-releasing hormone in a mammal in need thereof which comprises administering to said mammal an effective amount of a compound of the above [1] or a salt thereof with a pharmaceutically acceptable excipient, carrier or diluent;

[17] use of a compound of the above [1] or a salt thereof for manufacturing a pharmaceutical composition for antagonizing gonadotropin-releasing hormone, and so forth.

Each symbol in the above formulae is hereinafter described in more detail.

The "$C_{1-4}$ alkoxy group" for R¹ or R² includes, for example, methoxy, ethoxy, propoxy, butoxy, isopropoxy, t-butoxy, etc. Among others, preferred is $C_{1-3}$ alkoxy. More preferred is methoxy.

The "$C_{1-4}$ alkoxy-carbonyl group" for $R^1$ or $R^2$ includes, for example, methoxycarbonyl, ethoxycarbonyl, propoxycarbonyl, isopropoxycarbonyl, butoxycarbonyl, t-butoxycarbonyl, etc. Among others, preferred is $C_{1-3}$ alkoxy-carbonyl. More preferred is methoxycarbonyl.

The "$C_{1-4}$ alkyl group" of the "$C_{1-4}$ alkyl group which may be substituted" for $R^1$ or $R^2$ includes, for example, a straight-chain $C_{1-4}$ alkyl group (e.g., methyl, ethyl, propyl, butyl, etc.), a branched $C_{3-4}$ alkyl group (e.g., isopropyl, isobutyl, sec-butyl, tert-butyl, etc.), and so forth. Among others, preferred is a $C_{1-3}$ alkyl group. More preferred is ethyl.

The "substituents" of the "$C_{1-4}$ alkyl group which may be substituted" for $R^1$ or $R^2$ include, for example, (i) hydroxy, (ii) $C_{1-7}$ acyloxy (e.g., $C_{1-6}$ alkyl-carbonyloxy such as acetoxy, propionyloxy, etc.), (iii) benzoyloxy, (iv) amino which may be substituted by 1 or 2 substituents selected from the group consisting of $C_{1-6}$ alkoxy-carbonyl (e.g., methoxycarbonyl, ethoxycarbonyl, tert-butoxycarbonyl, etc.), benzyloxycarbonyl, $C_{1-4}$ acyl (e.g., $C_{1-3}$ alkylcarbonyl such as acetyl, propionyl, etc.), $C_{1-4}$ alkyl (e.g., methyl, ethyl, propyl, butyl, etc.) and $C_{1-3}$ alkylsulfonyl (e.g., methanesulfonyl etc.), etc. [e.g., amino, dimethylamino, methoxycarbonylamino, ethoxycarbonylamino, tert-butoxycarbonylamino, benzyloxycarbonylamino, acetylamino, methanesulfonylamino, etc.], (v) $C_{1-10}$ alkoxy (e.g., methoxy, ethoxy, propoxy, tert-butoxy, etc.), (vi) $C_{3-7}$ cycloalkyloxycarbonyl-$C_{1-3}$ alkoxy (e.g., cyclohexyloxycarbonyloxy-1-ethoxy, etc.), (vii) $C_{1-3}$ alkoxy-$C_{1-3}$ alkoxy (e.g., methoxymethoxy, methoxyethoxy, etc.), and so forth. Among others, preferred is hydroxy.

The "$C_{1-4}$ alkyl group" of the "$C_{1-4}$ alkyl group which may be substituted" for $R^1$ or $R^2$ may have 1 to 5, preferably 1 to 3, substituents as mentioned above at possible positions and, when the number of substituents is two or more, those substituents may be the same as or different from one another.

Preferably, one of $R^1$ and $R^2$ is a hydrogen atom, and the other is a $C_{1-3}$ alkoxy group.

The "halogen atom" for $R^3$ includes, for example, fluoro, chloro, bromo, iodo, etc. Among others, preferred is chloro.

The "$C_{1-4}$ alkoxy group" of the "$C_{1-4}$ alkoxy group which may be substituted" for $R^3$ includes, for example, methoxy, ethoxy, propoxy, isopropoxy, butoxy, t-butoxy, etc. Among others, preferred is methoxy.

The "substituents" of the "$C_{1-4}$ alkoxy group which may be substituted" for $R^3$ are the same as those mentioned above for the "substituents" of the "$C_{1-4}$ alkyl group which may be substituted" for $R^1$ or $R^2$. Among others, preferred is a $C_{1-4}$ alkoxy group.

The "$C_{1-4}$ alkoxy group" may have 1 to 5, preferably 1 to 3, substituents as mentioned above at possible positions and, when the number of substituents is two or more, those substituents may be the same as or different from one another.

The "$C_{1-4}$ alkylenedioxy group" formed by adjacent two $R^3$ includes, for example, methylenedioxy, ethylenedioxy, etc.

$R^3$ is preferably a hydrogen atom.

The "$C_{1-4}$ alkyl group" for $R^4$ includes, for example, a straight-chain $C_{1-4}$ alkyl group (e.g., methyl, ethyl, propyl, butyl, etc.), a branched $C_{3-4}$ alkyl group (e.g., isopropyl, isobutyl, sec-butyl, tert-butyl, etc.), and so forth. Among others, preferred is a $C_{1-3}$ alkyl group. More preferred is methyl.

The "$C_{1-4}$ alkyl group which may be substituted" for $R^6$ are the same as those mentioned above for the "$C_{1-4}$ alkyl group which may be substituted" for $R^1$ or $R^2$.

The "heterocycle" formed by $R^4$ and $R^5$ includes, for example, a 5- or 6-membered N-containing heterocycle, etc. When $R^4$ and $R^5$ form, taken together, examples of the group of the formula:

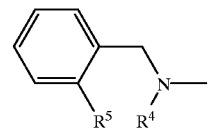

include a group of the formula:

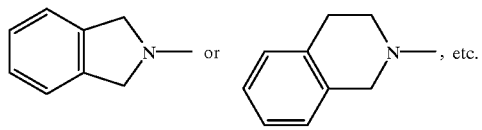

Among others, preferred is a group of the formula:

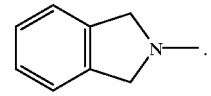

Preferably, $R^6$ is a group of the formula:

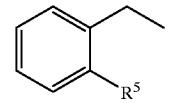

wherein $R^5$ is as defined above.

Preferably, $R^4$ is $C_{1-3}$ alkyl and $R^5$ is a hydrogen atom.

Preferably, n is 1 or 2.

Preferable examples of compound (I) include a compound (Ia).

More preferred is a compound or a salt thereof, wherein $R^1$ is a hydroxy group, a methoxy group or a $C_{1-3}$ alkyl group; $R^2$ is a hydrogen atom or a $C_{1-3}$ alkyl group; $R^4$ is a $C_{1-3}$ alkyl group; $R^6$ is a benzyl group; and n is 0.

Among others, more preferred is a compound or a salt thereof, wherein $R^1$ is a $C_{1-3}$ alkoxy group; $R^2$ and $R^5$ each is a hydrogen atom; R4 is a $C_{1-3}$ alkyl group; $R^6$ is a benzyl group; and n is 0.

Other preferable examples of compound (I) include a compound or a salt thereof, wherein $R^1$ is (i) a hydroxy group, (ii) a $C_{1-4}$ alkoxy group, or (iii) a $C_{1-4}$ alkyl group which may be substituted by hydroxy or $C_{1-4}$ alkyl-carbonyloxy; $R^2$ is a hydrogen atom, a $C_{1-4}$ alkyl group or a $C_{1-4}$ alkoxycarbonyl group; $R^3$ is a hydrogen atom, a halogen atom, a hydroxy group or a $C_{1-4}$ alkoxy-$C_{1-4}$ alkoxy group; or adjacent two $R^3$ form, taken together, a $C_{1-3}$ alkylenedioxy group; $R^4$ is a hydrogen atom or a $C_{1-3}$ alkyl group; $R^6$ is a $C_{1-4}$ alkoxy-$C_{1-4}$ alkyl group or a group of the formula:

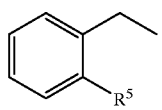

wherein $R^5$ is a hydrogen atom or $R^4$ and $R^5$ form, taken together, a 5- or 6-membered heterocycle; and n is 1 or 2.

As compound (I), concretely mentioned are 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione or a salt thereof, 5-(N-benzyl-N-methylaminomethyl)-1-(2,6-difluorobenzyl)-6-[4-(3-hydroxyureido)phenyl]-3-phenylthieno[2,3-d]pyrimidine-2,4(1H,3H)-dione or a salt thereof, 5-(N-benzyl-N-methylaminomethyl)-1-(2,6-difluorobenzyl)-6-[4-(3-methylureido)phenyl]-3-phenylthieno[2,3-d]pyrimidine-2,4(1H,3H)-dione or a salt thereof, 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione or a salt thereof, and so forth.

Among others, preferred is 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione or a salt thereof.

Salts of compound (I) are preferably physiologically acceptable acid addition salts. Such salts include, for example, salts with inorganic acids (e.g.,hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), and so forth. When compound (I) has an acidic group, it may form a physiologically acceptable salt with an inorganic base (e.g., alkali metals and alkaline earth metals such as sodium, potassium, calcium and magnesium, ammonia) or an organic base (e.g., trimethylamine, triethylamine, pyridine, picoline, ethanolamine, diethanolamine, triethanolamine, dicyclohexylamine, N,N'-dibenzylethylenediamine, etc).

Compound (I) can be produced in any per se known manner, for example, according to the methods disclosed in JP-A-9-169768, WO 96/24597 or analogous methods thereto. Concretely mentioned are the following Production method 1 and Production method 2. Compounds (II) to (VII) described in the following process include their salts. For their salts, for example, referred to are the same as the salts of compound (I).

Production Method 1

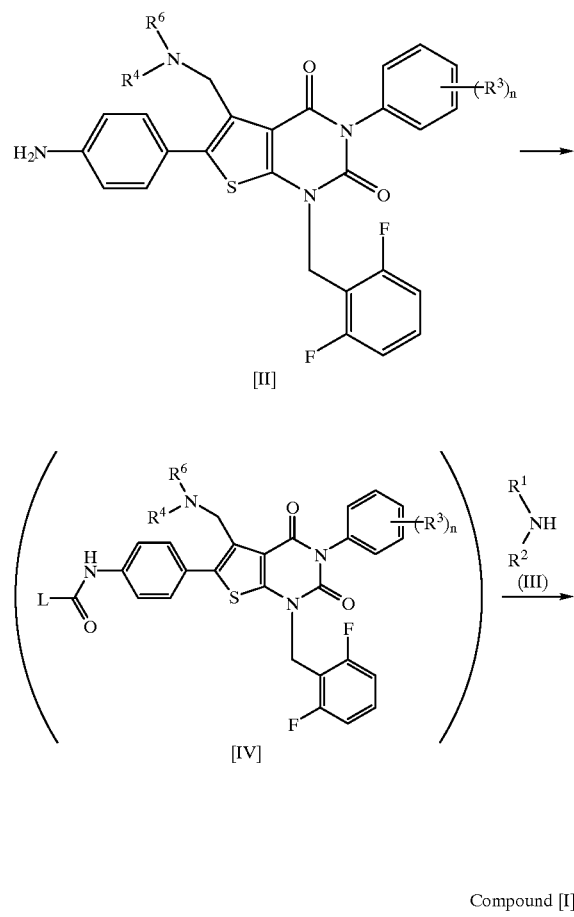

Compound [I]

In the above formulae, L represents a leaving group, and other symbols are as defined above.

The "leaving group" for L includes, for example, 1-imidazolyl, halogen, an alkoxy group which may be substituted, etc. The "alkoxy group which may be substituted" includes, for example, a $C_{1-4}$ alkoxy group which may be substituted by 1 to 3 halogen such as chloro, bromo, etc. (e.g., 2,2,2-trichloroethoxy, etc.).

Compound (II) can be produced by the methods disclosed in JP-A-9-169768 or analogous methods thereto.

Compound (I) can be produced by reacting compound (II) with carbonyldiimidazole (N,N'-carbonyldiimidazole; CDI) or phosgene (monomer, dimer or trimer) to obtain compound (IV), followed by reacting with compound (III). The reaction can be carried out without isolation of compound (IV), or compound (IV) can be used as a purified form in the next reaction.

Compound (IV) can also be produced by reacting compound (II) with, for example, a chloroformic acid ester compound (e.g., chloroformic acid 2,2,2-trichloroethyl ester, chloroformic acid 1-chloroethyl ester, etc.).

In the reaction of compound (II) with carbonyldiimidazole or phosgene, etc., carbonyldiimidazole or phosgene, etc. is used in amount of about 1 to 3 moles, relative to one mole of compound (II).

This reaction is advantageously carried out in a solvent inert to the reaction.

Examples of the solvent include ethers (e.g., ethyl ether, dioxane, dimethoxyethane, tetrahydrofuran, etc.), aromatic hydrocarbons (e.g., benzene, toluene, etc.), amides (e.g., dimethylformamide, dimethylacetamide, etc.), halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 36 hours.

This reaction is also carried out in the presence of a base. The "base" is exemplified by inorganic bases such as sodium carbonate, sodium hydrogencarbonate, potassium carbonate, potassium hydrogencarbonate, sodium hydroxide, potassium hydroxide and thallium hydroxide, and organic bases such as triethylamine and pyridine, etc.

The amount of the "base" is about 2 to 20 moles, preferably about 5 to 12 moles, relative to one mole of compound (II).

The following reaction with compound (III) can be carried out in the same condition as the above reaction of compound (II) with carbonyldiimidazole or phosgene. The amount of compound (III) is about 2 to 20 moles, preferably about 5 to 10 moles, relative to one mole of compound (II) or compound (IV). The reaction temperature is usually about 0 to 150° C., preferably room temperature (about 15 to 25° C.). The reaction time is usually about 1 to 6 hours.

Compound (III) and carbonyldiimidazole or phosgene can be reacted with compound (II) at the same time.

Production Method 2

In the above formulae, $R^7$ represents a hydrogen atom or an alkyl group, $R^8$ represents an alkyl group, and other symbols are as defined above.

The "$C_{1-4}$ alkyl group" for $R^7$ or $R^8$ includes, for example, the "$C_{1-4}$ alkyl group" of the "$C_{1-4}$ alkyl group which may be substituted" for $R^1$ or $R^2$.

Compound (V) can be produced in any per se known manner, for example, p-nitrophenylacetone is reacted with a cyanoacetic ester compound and sulphur [e.g., Chem. Ber., 99, 94–100(1966)], and thus obtained 2-amino-4-methyl-5-(4-nitrophenyl)thiophene is subjected to the methods disclosed in JP-A-9-169768, WO 96/24597 or analogous methods thereto.

1) When $R^7$ is a hydrogen atom, compound (I) can be produced by reacting compound (V) with a compound of the formula:

(VI)

wherein each symbol is as defined above, or a salt thereof [hereinafter sometimes referred to briefly as compound (VI)], in the presence of a condensing agent, to obtain compound (VII), following by subjecting to cyclization.

The "condensing agent" includes, for example, benzotriazol-1-yloxytripyrrolidinophosphonium hexafluorophosphate (PyBOP), etc.

The amount of the "condensing agent" is about 1 to 3 moles, relative to one mole of compound (V).

This reaction is advantageously carried out in a solvent inert to the reaction.

Examples of the solvent include alcohols (e.g., ethanol, methanol, etc.), aromatic hydrocarbons (e.g., benzene, toluene, etc.), amides (e.g., dimethylformamide, dimethylacetamide, etc.), halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 36 hours.

The product as produced in the manner mentioned above may be applied to the next reaction while it is still crude in the reaction mixture, or may be isolated from the reaction mixture in any ordinary manner.

Compound (VII) is subjected to cyclization in the presence of a base.

The "base" is exemplified by inorganic bases such as sodium methoxide, sodium carbonate, sodium hydrogencarbonate, potassium carbonate, potassium hydrogencarbonate, sodium hydroxide, potassium hydroxide and thallium hydroxide, and organic bases such as triethylamine and pyridine, etc.

The amount of the "base" is about 2 to 20 moles, preferably about 5 to 12 moles, relative to one mole of compound (VII).

This reaction is advantageously carried out in a solvent inert to the reaction.

Examples of the solvent include alcohols (e.g., ethanol, methanol, etc.), aromatic hydrocarbons (e.g., benzene, toluene, etc.), amides (e.g., dimethylformamide, dimethylacetamide, etc.), halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 36 hours.

2) When $R^7$ is an alkyl group, compound (I) can be produced by reacting compound (V) with an activated compound (VI).

The activated compound (VI) can be produced in any per se known manner, for example, by reacting an organoaluminum reagent with compound (VI) in a solvent inert to the reaction.

The "organo-aluminum reagent" includes, for example, trimethyl aluminum, dimethyl aluminum chloride, etc, and a solution including them, etc.

The amount of the "organo-aluminum reagent" is about 1 to 5 moles, preferably about one mole, relative to one mole of compound (VI).

Examples of the solvent include halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 6 hours.

The cyclization can be carried out by reacting compound (V) with an activated compound (VI) to obtain compound (I).

The amount of the "compound (V)" is about ⅕ volume of a mixture of compound (VI) and the organo-aluminum reagent.

This reaction is advantageously carried out in a solvent inert to the reaction.

Such solvent is the same as those used in the reaction to obtain an activated compound (VI).

The reaction temperature is usually about 0 to 150° C., preferably room temperature (about 15 to 25° C.). The reaction time is usually about 1 to 48 hours.

Compound (I) may be isolated and purified by ordinary means of separation such as recrystallization, distillation and chromatography, etc.

When compound (I) is obtained in free form, it can be converted to a salt by per se known methods or analogous thereto. When compound (I) is obtained in salt form, it can be converted to the free form or another salt by per se known methods or analogous thereto.

Compound (I) may be a hydrate or a non-hydrate. The hydrate is exemplified by monohydrate, sesquihydrate and dihydrate.

When compound (I) is obtained as a mixture of optically active configurations, it can be resolved into the (R)- and (S)-forms by the conventional optical resolution techniques.

Compound (I) may be labeled by an isotope (e.g., $^3$H, $^{14}$C, $^{35}$S, etc.).

Compound (I) of the present invention (hereinafter also referred to as "compound of the present invention") possesses excellent GnRH-antagonizing activity and low toxicity. In addition, it is excellent in oral absorbability, action sustainability, stability and pharmacokinetics. Furthermore, it can be easily produced. The compound of the present invention can therefore be safely used in a mammal (e.g., human, monkey, bovine, horse, dog, cat, rabbit, rat, mouse, etc.) for the preventing and/or treating diseases depending on male or female hormones, diseases due to excess of these hormones, etc., by suppressing gonadotropin secretion by its GnRH receptor-antagonizing action to control plasma sex hormone concentrations.

For example, the compound of the present invention is useful for preventing and/or treating sex hormone-dependent cancers (e.g., prostatic cancer, uterine cancer, breast cancer, pituitary tumor, etc.), prostatic hypertrophy, hysteromyoma, endometriosis, precocious puberty, amenorrhea, premenstrual syndrome, multilocular ovary syndrome, pimples etc. The compound of the present invention is also useful for the regulation of reproduction in males and females (e.g., pregnancy regulators, menstruation cycle regulators, etc.). The compound of the present invention also be used as a male or female contraceptive, or as a female ovulation inducer. Based on its rebound effect after withdrawal, the compound of the present invention can be used to treat infertility.

In addition, the compound of the present invention is useful for regulation of animal estrous, improvement of meat quality and promotion of animal growth in the field of animal husbandry. The compound of the present invention is also useful as a fish spawning promoter.

The compound of the present invention can also be used to suppress the transient rise in plasma testosterone concentration (flare phenomenon) observed in administration of a GnRH super-agonist such as leuprorelin acetate. The compound of the present invention can be used in combination with a GnRH super-agonist such as leuprorelin acetate, gonadrelin, buserelin, triptorelin, goserelin, nafarelin, histrelin, deslorelin, meterelin, lecirelin, and so forth. Among others, preferred is leuprorelin acetate.

It is also beneficial to use the compound of the present invention in conjunction (in combination or concomitantly) with at least one member selected from among the steroidal or nonsteroidal androgen antagonist or antiestrogen, chemotherapeutic agent, GnRH antagonistic peptide, α-reductase inhibitor, α-receptor inhibitor, aromatase inhibitor, 17β-hydroxysteroid dehydrogenase inhibitor, adrenal androgen production inhibitor, protein kinase inhibitor, drug for hormone therapy, and drug antagonizing growth factor or its receptor, among others.

The "chemotherapeutic agent" mentioned above includes ifosfamide, UTF, adriamycin, peplomycin, cisplatin, cyclophosphamide, 5-FU, UFT, methotrexate, mitomycin C, mitoxantrone, etc.

The "GnRH antagonistic peptide" mentioned above includes non-oral GnRH antagonistic peptides such as cetrorelix, ganirelix, abarelix, etc.

The "adrenal androgen production inhibitor" mentioned above includes lyase ($C_{17,20}$-lyase) inhibitors, etc.

The "protein kinase inhibitor" mentioned above includes tyrosine kinase inhibitor, etc.

The "drugs for hormone therapy" includes antiestrogens, progesterons (e.g., MPA, etc.), androgens, estrogens and androgen antagonists, among others.

The "growth factor" may be any substance that promotes proliferation of cells and generally includes peptides with molecular weights not over 20,000 which express the action at low concentrations through binding to receptors. Specifically, there can be mentioned (1) EGF (epidermal growth factor) or substances having the substantially the same activity (e.g., EGF, heregulin (HER2ligand), etc.), (2) insulin or substances having substantially the same activity (e.g., insulin, IGF (insulin-like growth factor)-1, IGF-2, etc.), (3) FGF (fibroblast growth factor) or substances having substantially the same activity (aFGF, bFGF, KGF (keratinocyte growth factor), HGF (hepatocyte growth factor), FGF-10, etc.), and (4) other growth factors (e.g., CSF (colony stimulating factor), EPO (erythropoietin), IL-2 (interleukin-2), NGF (nerve growth factor), PDGF (platelet-derived growth factor) and TGFβ (transforming growth factor β), etc.), among others.

The "growth factor receptor" mentioned above may be any receptor capable of binding said growth factor, including EGF receptor, heregulin receptor (HER2), insulin receptor-1, insulin receptor-2, IGF receptor, FGF receptor-1, FGF receptor-2, etc.

The drug antagonizing said growth factor includes herceptin (anti-HER2 receptor antibody), among others.

The drug antagonizing said growth factor or growth factor receptor includes herbimycin, PD153035 [e.g., Science, 265 (5175) p1093, (1994)], etc. can be mentioned.

As a further class of drugs antagonizing said growth factor or growth factor receptor includes HER2 antagonists.

The HER2 antagonist may be any substance that inhibits the activity of HER2 (e.g., phosphorylating activity), thus including an antibody, a low-molecular compound (synthetic or natural product), an antisense, an HER2 ligand, heregulin, and any of them as partially modified or mutated in structure. Moreover, it may be a substance which inhibits HER2 activity by antagonizing HER2 receptor (e.g. HER2 receptor antibody). The low molecular compound having HER2 antagonizing activity includes, for example, the compounds described in WO 98/03505, namely 1-[3-[4-[2-((E)-2-phenylethenyl)-4-oxazolylmethoxy]phenyl]propyl]-1,2,4-triazole and so on.

For prostatic hypertrophy, examples of such combination includes the compound of the present invention in combination with the GnRH super-agonist, androgen antagonist, antiestrogen, GnRH antagonistic peptide, α-reductase inhibitor, α-receptor inhibitor, aromatase inhibitor, 17β-hydroxysteroid dehydrogenase inhibitor, adrenal androgen production inhibitor, phosphorylase inhibitor, and so forth.

For prostatic cancer, examples of such combination includes the compound of the present invention in combination with the GnRH super-agonist, androgen antagonist, antiestrogen, chemotherapeuticagent (e.g., ifosfamide, UTF, adriamycin, peplomycin, cisplatin, etc.), GnRH antagonistic peptide, aromatase inhibitor, 17β-hydroxysteroid dehydrogenase inhibitor, adrenal androgen production inhibitor, phosphorylase inhibitor, drug for hormone therapy such as estrogens (e.g., DSB, EMP, etc.), androgen antagonist (e.g., CMA. etc.), drug antagonizing growth factor or its receptor, and so forth.

For breast cancer, examples of such combination includes the compound of the present invention in combination with the GnRH super-agonist, chemotherapeutic agent (e.g., cyclophosphamide, 5-FU, UFT, methotrexate, adriamycin, mitomycin C, mitoxantrone, etc.), GnRH antagonistic peptide, aromatase inhibitor, adrenal androgen production inhibitor, phosphorylase inhibitor, drug for hormone therapy such as antiestrogen (e.g., tamoxifen, etc.), progesterons (e.g., MPA, etc.), androgens, estrogens, etc., drug antagonizing growth factor or its receptor, and so forth.

When the compound of the present invention is used as a prophylactic and/or therapeutic agent for the above-mentioned diseases or used in the field of animal husbandry or fishery, it can be administered orally or non-orally, as formulated with a pharmaceutically acceptable carrier, normally in the form of solid preparations such as tablets, capsules, granules and powders for oral administration, or in the form of intravenous, subcutaneous, intramuscular or other injections, suppositories or sublingual tablets for non-oral administration. It may also be sublingually, subcutaneously, intramuscularly or otherwise administered in the form of sustained-release preparations of sublingual tablets, microcapsules etc. Depending on symptom severity; subject age, sex, weight and sensitivity; duration and intervals of administration; property, dispensing and kind of pharmaceutical preparation; kind of active ingredient etc., daily dose is not subject to limitation. For use in the treatment of the above-described sex hormone-dependent cancers (e.g., prostatic cancer, uterine cancer, breast cancer, pituitary tumor), prostatic hypertrophy, hysteromyoma, endometriosis, precocious puberty etc., daily dose is normally about 0.01 to 30 mg, preferably about 0.02 to 10 mg, and more preferably 0.1 to 10 mg, especially preferably 0.1 to 5 mg per kg weight of mammal, normally in 1 to 4 divided dosages.

The above doses are applicable to the use of the compound of the present invention in the field of animal husbandry or fishery. Daily dose is about 0.01 to 30 mg, preferably about 0.1 to 10 mg, per kg weight of subject organism, normally in 1 to 3 divided dosages.

In the pharmaceutical composition of the present invention, the amount of compound (I) is 0.01 to 100% by weight or so of the total weight of the composition.

The above pharmaceutically acceptable carriers are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary.

Preferable excipients include, for example, lactose, sucrose, D-mannitol, starch, crystalline cellulose and light silicic anhydride. Preferable lubricants include, for example, magnesium stearate, calcium stearate, talc and colloidal silica. Preferable binders include, for example, crystalline cellulose, sucrose, D-mannitol, dextrin, hydroxypropyl cellulose, hydroxypropylmethyl cellulose and polyvinylpyrrolidone. Preferable disintegrants include, for example, starch, carboxymethyl cellulose, carboxymethyl cellulose calcium, crosslinked carmellose sodium and carboxymethyl starch sodium. Preferable solvents include, for example, water for injection, alcohol, propylene glycol, macrogol, sesame oil and corn oil. Preferable dissolution aids include, for example, polyethylene glycol, propylene glycol, D-mannitol, benzyl benzoate, ethanol, trisaminomethane, cholesterol, triethanolamine, sodium carbonate and sodium citrate. Preferable suspending agents include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include, for example, sodium chloride, glycerol and D-mannitol. Preferable buffers include, for example, buffer solutions of phosphates, acetates, carbonates, citrates etc. Preferable soothing agents include, for example, benzyl alcohol. Preferable preservatives include, for example, paraoxybenzoic acid esters, chlorobutanol, benzyl alcohol, phenethyl alcohol, dehydroacetic acid and sorbic acid. Preferable antioxidants include, for example, sulfites and ascorbic acid.

By adding suspending agents, dissolution aids, stabilizers, isotonizing agents, preservatives, and so forth, the compound of the present invention can be prepared as an intravenous, subcutaneous or intramuscular injection by a commonly known method. In such cases, the compound of the present invention can be freeze-dried as necessary by a commonly known method. In administration to humans, for example, the compound of the present invention can be safely administered orally or non-orally as such or as a pharmaceutical composition prepared by mixing it with a pharmacologically acceptable carrier, excipient and diluent selected as appropriate.

Such pharmaceutical compositions include oral preparations (e.g., powders, granules, capsules, tablets), injections, drip infusions, external preparations (e.g., nasal preparations, transdermal preparations) and suppositories (e.g., rectal suppositories, vaginal suppositories).

These preparations can be produced by commonly known methods in common use for pharmaceutical making processes.

An injection can be produced by, for example, preparing the compound of the present invention as an aqueous injection along with a dispersing agent (e.g., Tween 80, produced by Atlas Powder Company, USA, HCO 60, produced by Nikko Chemicals Co., Ltd., polyethylene glycol, carboxymethyl cellulose, sodium alginate), a preservative (e.g., methyl paraben, propyl paraben, benzyl alcohol), an isotonizing agent (e.g., sodium chloride, mannitol, sorbitol, glucose) and other additives, or as an oily injection in solution, suspension or emulsion in a vegetable oil such as olive oil, sesame oil, cottonseed oil or corn oil, propylene glycol or the like.

An oral preparation can be produced by formulating the compound of the present invention by a commonly known method after addition of an excipient (e.g., lactose, sucrose, starch), a disintegrant (e.g., starch, calcium carbonate), a binder (e.g., starch, gum arabic, carboxymethyl cellulose, polyvinylpyrrolidone, hydroxypropyl cellulose), a lubricant (e.g., talc, magnesium stearate, polyethylene glycol 6000) and other additives, and, where necessary, coating the formulated product for the purpose of taste masking, enteric dissolution or sustained release by a commonly known method. Coating agents for this purpose include, for example, hydroxypropylmethyl cellulose, ethyl cellulose, hydroxymethyl cellulose, hydroxypropyl cellulose, polyoxyethylene glycol, Tween 80, PrulonicF68, cellulose acetate phthalate, hydroxypropylmethyl cellulose phthalate, hydroxymethyl cellulose acetate succinate, Eudragit (produced by Rohm Company, Germany; methacrylic acid/acrylic acid copolymer) and dyes (e.g., iron oxide, titanium dioxide). For an enteric preparation, an intermediate phase may be provided between the enteric phase and the drug-containing phase for the purpose of separation of the two phases by a commonly known method.

An external preparation can be produced by compounding the compound of the present invention as a solid, semi-solid or liquid composition by a commonly known method. Such a solid composition is produced by, for example, powdering the compound of the present invention as such or in mixture with an excipient (e.g., glycol, mannitol, starch, microcrystalline cellulose), a thickening agent (e.g., natural rubber, cellulose derivative, acrylic acid polymer) and other additives. Such a liquid composition is produced by preparing the compound of the present invention as an oily or aqueous suspension in almost the same manner as with the injection. The semi-solid composition is preferably an aqueous or oily gel, or an ointment. All these compositions may contain pH regulators (e.g., carbonic acid, phosphoric acid, citric acid, hydrochloric acid, sodium hydroxide), preservatives (e.g., paraoxybenzoic acid esters, chlorobutanol, benzalkonium chloride) and other additives.

A suppository is produced by preparing the compound of the present invention as an oily or aqueous solid, semi-solid or liquid composition by a commonly known method. Useful oily bases for such compositions include glycerides of higher fatty acids (e.g., cacao fat, uitepsols, produced by Dynamite Nobel Company, Germany), moderate fatty acids (e.g., MIGLYOL, produced by Dynamite Nobel Company, Germany), and vegetable oils (e.g., sesame oil, soybean oil, cottonseed oil). Aqueous bases include, for example, polyethylene glycols and propylene glycol. Bases for aqueous gels include, for example, natural rubbers, cellulose derivatives, vinyl polymers and acrylic acid polymers.

BEST MODE FOR CARRYING OUT THE INVENTION

The present invention is hereinafter described in more detail by means of, but is not limited to, the following reference examples, examples, preparation examples and experimental examples.

$^1$H-NMR spectra are determined with tetramethylsilane as the internal standard, using the Varian GEMINI 200 (200 MHz) spectrometer, the JEOL LAMBDA 300 (300 MHz) spectrometer or the Bruker AM500 (500MHz) spectrometer; all $\delta$ values are shown in ppm. Unless otherwise specifically indicated, "%" is by weight. Yield indicates mol/mol %.

The other symbols used herein have the following definitions:

s: singlet d: doublet t: triplet dt: double triplet m: multiplet br: broad

TFA: trifluoroacetic acid

THF: tetrahydrofuran

Me: methyl

Et: ethyl

The term "room temperature" indicates the range from about 15 to 25° C., but is not to be construed as strictly limitative.

EXAMPLES

Reference Example 1

Ethyl 2-amino-4-methyl-5-(4-nitrophenyl)thiophene-3-carboxylate

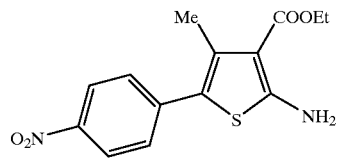

A mixture of 4-nitrophenylacetone (35.0 g, 195 mmol), ethyl cyanoacetate (23.8 g, 195 mmol), ammonium acetate (3.1 g, 40 mmol) and acetic acid (9.1 ml, 159 mmol) was heated on reflux for 24 hours, with removing water produced through the reaction with a Dean-Stark trap. After cooling, the reaction mixture was concentrated under reduced pressure and the residue was partitioned between dichloromethane and aqueous sodium hydrogencarbonate solution. The organic extract was washed with aqueous sodium chloride solution and dried (MgSO$_4$) and the solvent was distilled off under reduced pressure. The residue was chromatographed on silica gel to give oil compound. The oil thus obtained was dissolved in ethanol followed by addition of sulfur (5.0 g, 160 mmol) and diethylamine (16.0 ml, 160 mmol), and the mixture was stirred at 60 to 70° C. for 2 hours. After cooling, the reaction mixture was concentrated under reduced pressure to yield residue, which was partitioned between dichloromethane and aqueous sodium hydrogencarbonate solution. The organic extract was washed with aqueous sodium chloride solution and dried (MgSO$_4$) and the solvent was distilled off under reduced pressure. The residue was chromatographed on silica gel to give the crude product, which was recrystallized from ether-hexane to give the title compound as red plates (22.2 g, 52%).

mp: 168–170° C. (recrystallized from ether-hexane).

Elemental analysis for $C_{14}H_{14}N_2O_4S$

|  | C(%) | H(%) | N(%) |
|---|---|---|---|
| Calculated: | 54.89; | 4.61; | 9.14 |
| Found: | 54.83; | 4.90; | 9.09 |

$^1$H-NMR (200 MHz, CDCl$_3$) δ: 1.39 (3H, t, J=7.1 Hz), 2.40 (3H, s), 4.34 (2H, q, J=7.1 Hz), 6.27 (2H, br), 7.48 (2H, d, J=8.7 Hz), 8.23 (2H, d, J=8.7 Hz).

IR (KBr): 3446, 3324, 1667, 1580, 1545, 1506, 1491, 1475, 1410, 1332 cm$^{-1}$.

Reference Example 2

5-Methyl-6-(4-nitrophenyl)-3-phenylthieno[2,3-d]pyrimidine-2,4(1H,3H)-dione

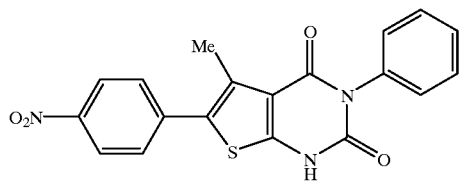

To a solution of the compound obtained in Reference Example 1 (5.00 g, 16.32 mmol) in pyridine (30 ml) was added phenyl isocyanate (2.66 ml, 24.48 mmol). After 6 hours of stirring at 45° C., the reaction mixture was concentrated under reduced pressure and the residue was dissolved in ethanol (6 ml). To this solution was added 28% sodium methoxide (7.86 g, 40.80 mmol), and the mixture was stirred at room temperature for 2 hours. Then, 2N-hydrochloric acid (25 ml, 50 mmol) was added and the solvent ethanol was distilled off under reduced pressure. The residue was filtered, washed with water-ethanol, dried in vacuo, and recrystallized from ethanol to give the title compound as yellow powder (6.09 g, 98%).

mp:>300° C.

Elemental analysis for $C_{19}H_{13}N_3O_4S \cdot 0.3H_2O$

|  | C(%) | H(%) | N(%) |
|---|---|---|---|
| Calculated: | 59.30; | 3.56; | 10.92 |
| Found: | 59.56; | 3.52; | 10.93 |

$^1$H-NMR (300 MHz, DMSO-d$_6$) δ: 2.50 (3H, s), 7.31–7.46 (5H, m), 7.78 (2H, d, J=8.8 Hz), 8.32 (2H, d, J=8.8 Hz), 12.50 (1H, s).

IR (KBr): 1715, 1657, 1593, 1510 cm$^{-1}$.

Reference Example 3

1-(2,6-Difluorobenzyl)-5-methyl-6-(4-nitrophenyl)-3-phenylthieno[2,3-d]pyrimidine-2,4(1H,3H)-dione

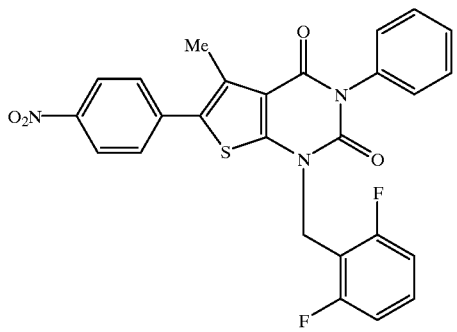

To a solution of the compound obtained in Reference Example 2 (52.54 g, 0.131 mmol) in N,N-dimethylformamide (1.0 L) were added potassium carbonate (19.00 g, 0.138 mol), potassium iodide (22.90 g, 0.138 mol) and 2,6-difluorobenzyl chloride (22.40 g, 0.138 mol), and the mixture was stirred at room temperature for 2 hours. This reaction mixture was concentrated under reduced pressure to give the residue, which was partitioned between chloroform and aqueous sodium chloride solution. The aqueous layer was extracted with chloroform. The combined extracts were washed with aqueous sodium chloride solution and dried (MgSO$_4$) and the solvent was distilled off under reduced pressure. The residue was chromatographed on silica gel to give the title compound as light-yellow crystals (61.50 g, 93%).

mp: 280–282° C.

Elemental analysis for $C_{26}H_{17}N_3O_4SF_2$

|  | C(%) | H(%) | N(%) |
|---|---|---|---|
| Calculated: | 61.78; | 3.39; | 8.31 |
| Found: | 61.67; | 3.46; | 8.21 |

$^1$H-NMR (300 MHz, CDCl$_3$) δ: 2.57 (3H, s), 5.38 (2H, s), 6.94 (2H, d, J=8.1 Hz), 7.42–7.58 (8H, m), 8.29 (2H, d, J=8.8 Hz).

IR (KBr): 1719, 1669, 1524, 1473 cm$^{-1}$.

Reference Example 4

5-Bromomethyl-1-(2,6-difluorobenzyl)-6-(4-nitrophenyl)-3-phenylthieno[2,3-d]pyrimidine-2,4(1H,3H)-dione

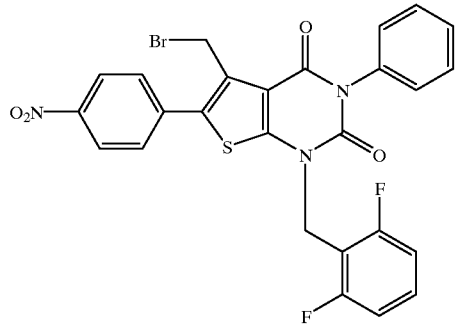

A mixture of the compound obtained in Reference Example 3 (30.34 g, 0.060 mol), N-bromosuccinimide (12.81 g, 0.072 mol), α,α'-azobisisobutyronitrile (1.15 g, 0.007 mol) and chlorobenzene (450 ml) was stirred at 85° C. for 3hours. After cooling, the reaction mixture was washed with aqueous sodium chloride solution and dried (MgSO$_4$) and the solvent was then distilled off under reduced pressure. The residue was recrystallized from ethyl acetate to give the title compound as yellow needles (80.21 g, 100%).

mp: 228–229° C.

$^1$H-NMR (300 MHz, CDCl$_3$) δ: 4.77 (2H, s), 5.38 (2H, s), 6.96 (2H, t, J=8.1 Hz), 7.29–7.58 (6H, m), 7.79 (2H, d, J=8.5 Hz), 8.35 (2H, d, J=8.5 Hz).

IR (KBr): 1721, 1680, 1524, 1473, 1348 cm$^{-1}$.

FAB-Mass m/z 584(MH)$^+$

Reference Example 5

5-(N-Benzyl-N-methylaminomethyl)-1-(2,6-difluorobenzyl)-6-(4-nitrophenyl)-3-phenylthieno[2,3-d]pyrimidine-2,4(1H,3H)-dione

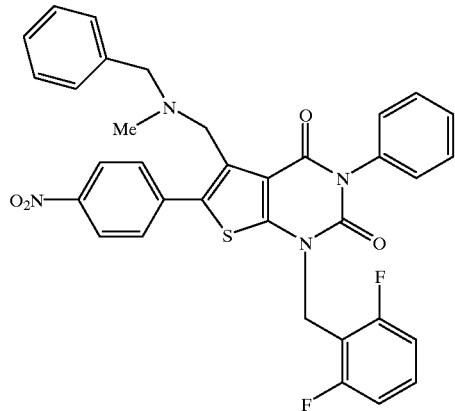

To a solution of the compound obtained in Reference Example 4 (80.00 g, 0.119 mol) in N,N-dimethylformamide (600 ml) were added ethyldiisopropylamine (27.00 ml, 0.155 mol) and benzylmethylamine(18.45 ml, 0.143 mol) with ice-cooling. After 2 hours of stirring at room temperature, the reaction mixture was concentrated and the residue was partitioned between ethyl acetate and saturated aqueous sodium hydrogencarbonate solution. The aqueous layer was extracted with ethyl acetate. The organic extracts were combined and dried (MgSO$_4$) and the solvent was distilled off under reduced pressure. The residue was chromatographed on silica gel to give a yellow oil (74.90 g, 100%), which was recrystallized from ethyl acetate to give the title compound as yellow needles.

mp: 173–174° C.

| Elemental analysis for C$_{34}$H$_{26}$N$_4$O$_4$SF$_2$.0.5H$_2$O | | | |
|---|---|---|---|
| | C(%) | H(%) | N(%) |
| Calculated: | 64.45; | 4.29; | 8.84 |
| Found: | 64.50; | 4.24; | 8.82 |

$^1$H-NMR (300 MHz, CDCl$_3$) [Free amine] δ: 1.31 (3H, s), 3.60 (2H, s),3.96 (2H, s), 5.39 (2H, s), 6.95 (2H, t, J=8.2 Hz), 7.18–7.55 (11H, m), 8.02 (2H, d, J=9.0 Hz), 8.26 (2H, d, J=9.0 Hz).

IR (KBr) [Hydrochloride] : 1719, 1678, 1597, 1520 cm$^{-1}$.

Reference Example 6

6-(4-Aminophenyl)-5-(N-benzyl-N-methylaminomethyl)-1-(2,6-difluorobenzyl)-3-phenylthieno[2,3-d]pyrimidine-2,4(1H,3H)-dione

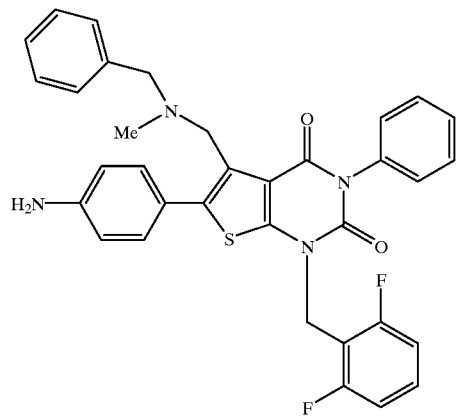

To a solution of the compound obtained in Reference Example 5 (3.00 g, 4.80 mmol) in formic acid (30 ml) were added 1M hydrogen chloride solution in ether (14.4 ml, 14.4 mmol) and 10% palladium-on-carbon (300 mg) with ice-cooling, and hydrogenation was carried out under atmospheric condition at room temperature with constant stirring for 2 hours. This reaction mixture was filtered through Celite and the filtrate was concentrated under reduced pressure. The residue was partitioned between dichloromethane and saturated aqueous sodium hydrogencarbonate solution. The aqueous layer was extracted with dichloromethane and the organic extracts were combined and dried (MgSO$_4$). The solvent was then distilled off under reduced pressure. The residue was chromatographed on silica gel to give the title compound as white crystals (2.41 g, 84%).

mp: 205–207° C.

| Elemental analysis for $C_{34}H_{28}N_4O_5SF_2.0.1AcOEt.1.2H_2O$ | | | |
|---|---|---|---|
| | C(%) | H(%) | N(%) |
| Calculated: | 66.09; | 5.03; | 8.96 |
| Found: | 66.93; | 4.94; | 8.67 |

$^1$H-NMR (300 MHz, CDCl$_3$) δ: 2.05(3H, s), 3.56(2H, s), 3.83(2H, br), 3.88(2H, s), 5.36(2H, s), 6.70(2H, d, J=8.8 Hz), 6.88–6.94(2H, m), 7.21–7.31(8H, m), 7.41–7.53(5H, m).

IR (KBr): 1715, 1657, 1628, 1537 cm$^{-1}$.

Reference Example 7

5-Chloromethyl-1-(2,6-difluorobenzyl)-6-[4-(3-methoxyureido)phenyl]-3-phenylthieno[2,3-d]pyrimidine-2,4(1H,3H)-dione

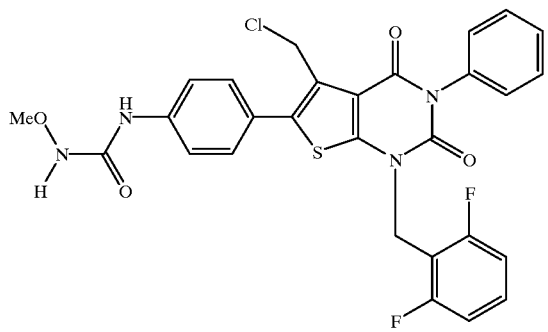

To a solution of the Example Compound No. 1 described below (2.00 g, 3.00 mmol) in tetrahydrofuran (90 ml) was added 1-chloroethyl chloroformate (0.42 ml, 3.89 mmol) at −78° C. The reaction mixture was allowed to warm to room temperature, the mixture was stirred for 2 hours. This reaction mixture was partitioned between chloroform and aqueous sodium chloride solution and the aqueous layer was extracted with chloroform. The extracts were combined, washed with aqueous sodium chloride solution and dried (MgSO$_4$) and the solvent was distilled off under reduced pressure. The residue was chromatographed on silica gel to give the title compound as white powder (1.68 g, 96%).

mp: 217–219° C.

$^1$H-NMR (300 MHz, CDCl$_3$) δ: 3.83 (3H, s), 4.84 (2H, s), 5.37 (2H, s), 6.94 (2H, t, J=8.2 Hz), 7.15 (1H, S), 7.28–7.65 (11H, m).

IR (KBr): 1717, 1671, 1628, 1541, 1508, 1473 cm$^{-1}$.

FAB-Mass m/z 583(MH)$^+$

Reference Example 8

Using the compound obtained in Reference Example 6 as a starting material, the following Reference Example Compounds No. 8-1 to 8-3 were obtained in the same manner as Examples 1 and 2 described below.

Reference Example Compound No. 8-1

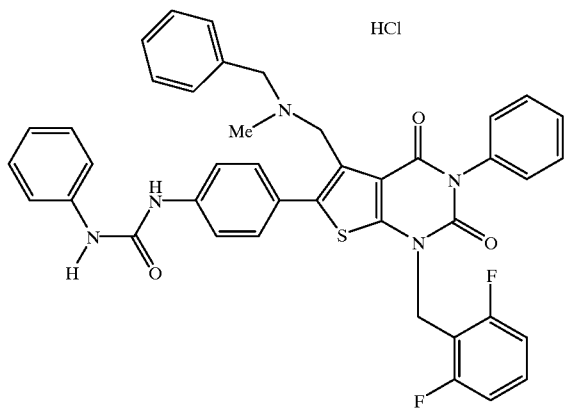

Yield: 64%
mp: 190–194° C.

Reference Example Compound No. 8-2

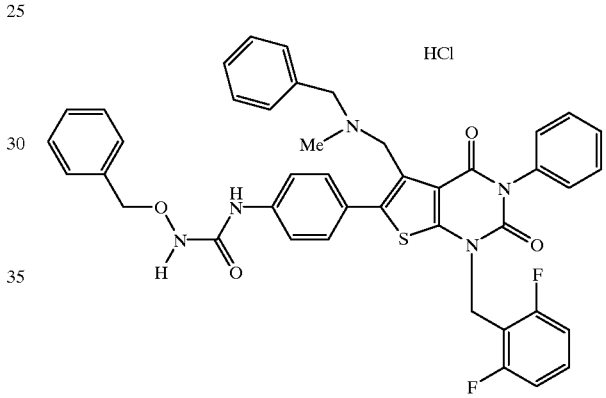

Yield: 91%
mp: 210–215° C.

Reference Example Compound No. 8-3

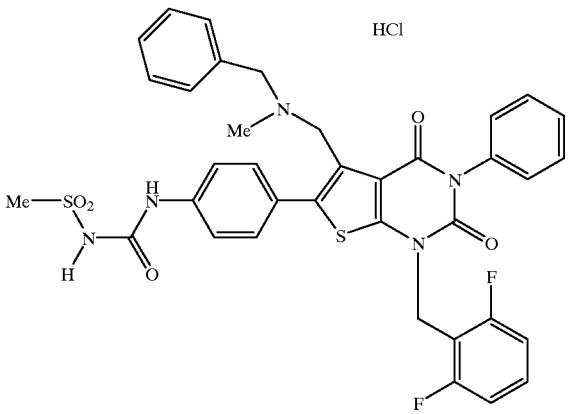

Yield: 82%
mp: 254–257° C.

Reference Example 9

Ethyl 2-ethoxycarbonylamino-4-methyl-5-(4-nitrophenyl)thiophene-3-carboxylate

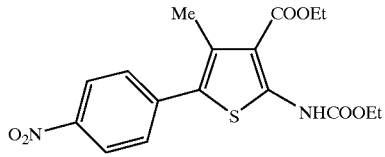

The compound obtained in Reference Example 1 (500 mg, 1.63 mmol) was dissolved in toluene (9 ml) followed by addition of ethyl chloroformate (0.19 ml, 1.96 mmol), and the mixture was heated under reflux for 5 hours. After cooling, the reaction mixture was concentrated under reduced pressure. The residue was chromatographed on silica gel to give the title compound as yellow powder (90 mg, 79%).

mp: 130–131° C. (recrystallized from ethyl acetate-hexane).

$^1$H-NMR (200 MHz, CDCl$_3$) δ: 1.35 (3H, t, J=7.1 Hz), 1.42 (3H, t, J=7.2 Hz), 2.42 (3H, s), 4.31 (2H, q, J=7.1 Hz), 4.39 (2H, q, J=7.2 Hz), 7.59 (2H, d, J=9.0 Hz), 8.27 (2H, d, J=9.0 Hz), 10.66 (1H, s).

IR (KBr): 1740, 1665, 1597, 1557, 1533, 1516, 1352, 1257 cm$^{-1}$.

Reference Example 10

Ethyl 2-[N-(2,6-difluorobenzyl)-N-ethoxycarbonylamino]-4-methyl-5-(4-nitrophenyl)thiophene-3-carboxylate

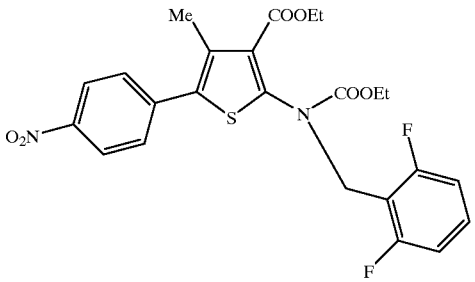

To a solution of the compound obtained in Reference Example 9 (490 mg, 1.30 mol) in N,N-dimethylformamide (20 ml) were added potassium carbonate (196 mg, 1.42 mol), potassium iodide (236 mg, 1.42 mol) and 2,6-difluorobenzyl chloride (232 mg, 1.42 mmol), and the mixture was stirred at room temperature for 5 hours. This reaction mixture was concentrated and the residue was partitioned between chloroform and aqueous sodium chloride solution. The aqueous layer was extracted with chloroform. The organic extracts were combined and washed with aqueous sodium chloride solution and dried (MgSO$_4$) and the solvent was distilled off under reduced pressure. The residue was chromatographed on silica gel and the amorphous powder obtained was recrystallized from methanol to give the title compound as yellow powdery crystals (520 mg, 79%).

mp: 91–92° C.

$^1$H-NMR (300 MHz, CDCl$_3$) δ: 1.15–1.35 (6H, m), 2.40 (3H, s), 4.15–4.29 (4H, m), 4.97 (2H, s), 6.86 (2H, t, J=7.8 Hz), 7.25–7.32 (1H, m), 7.51 (2H, d, J=8.8 Hz), 8.25 (2H, d).

IR (KBr): 1717, 1597, 1524, 1475, 1392, 1348 cm$^{-1}$.

Reference Example 11

Ethyl 4-bromomethyl-2-[N-(2,6-difluorobenzyl)-N-ethoxycarbonylamino]-5-(4-nitrophenyl)thiophene-3-carboxylate

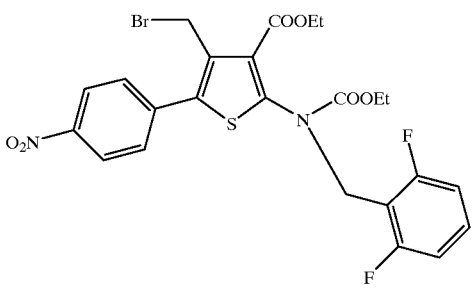

A mixture of the compound obtained in Reference Example 10 (20 g, 39.64 mol), N-bromosuccinimide (7.76 g, 43.60 mol), α,α'-azobisisobutyronitrile (0.72 g, 4.36 mol) and carbon tetrachloride (300 ml) was stirred at 100° C. for 2 hours. After cooling, this reaction mixture was washed with aqueous sodium chloride solution and dried (MgSO$_4$) and the solvent was distilled off under reduced pressure. The residue was chromatographed on silica gel to give the title compound as amorphous powder (23 g, 100%).

mp: 105–108° C.

$^1$H-NMR (300 MHz, CDCl$_3$) δ: 1.15–1.39 (6H, m), 4.09–4.39 (4H, m), 4.71 (2H, s), 4.99 (2H, s), 6.86 (2H, t, J=7.8 Hz), 7.22–7.32 (1H, m), 7.72 (2H, d, J=8.0 Hz), 8.32 (2H, d, J=8.0 Hz).

IR (KBr): 1725, 1628, 1522, 1475, 1379, 1348 cm$^{-1}$.

FAB-Mass m/z 582 (MH$^+$).

Reference Example 12

Ethyl 4-(N-benzyl-N-methylaminomethyl)-2-[N-(2,6-difluorobenzyl)-N-ethoxycarbonylamino]-5-(4-nitrophenyl)thiophene-3-carboxylate

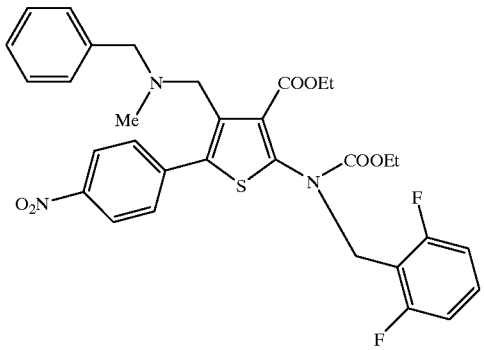

To a solution of the compound obtained in Reference Example 11 (2.0 g, 3.43 mmol) in N,N-dimethylformamide (20 ml) were added ethyldiisopropylamine (0.90 ml, 5.15 mmol) and benzylmethylamine (0.53 ml, 4.11 mmol) with ice-cooling, and the mixture was stirred at room temperature for 3 hours. This reaction mixture was concentrated and the residue was partitioned between ethyl acetate and saturated aqueous sodium hydrogencarbonate solution. The aqueous layer was extracted with ethyl acetate. The organic extracts were combined and dried (MgSO$_4$) and the solvent was distilled off under reduced pressure. The residue was chromatographed on silica gel to give the title compound as yellow oil (2.1 g, 48%).

$^1$H-NMR (300 MHz, CDCl$_3$) 67 : 1.18–1.44 (6H, m), 1.95 (3H, s), 3.27 (2H, s), 3.70 (2H, s), 4.20–4.32 (4H, m), 5.03 (2H, s), 6.80 (2H, t, J=7.8 Hz), 7.10–7.27 (6H, m), 7.52 (2H, d, J=8.0 Hz), 8.24 (2H, d, J=8.0 Hz).

IR (KBr) 1719, 1628, 1597, 1522, 1473, 1402, 1377, 1348 cm$^{-1}$.

Reference Example 13

Ethyl 5-(4-aminophenyl)-4-(N-benzyl-N-methylaminomethyl)-2-[N-(2,6-difluorobenzyl)-N-ethoxycarbonylamino]thiophene-3-carboxylate

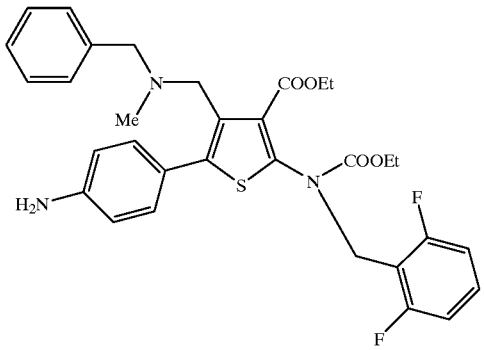

To a solution of the compound obtained in Reference Example 12 (10.0 g, 16.03 mmol) in formic acid (100 ml) were added 1M HCl solution in ether (48 ml, 48 mmol) and 10% palladium-on-carbon (1000 mg) with ice-cooling; and hydrogenation was carried out under atmospheric conditions at room temperature for 5 hours. This reaction mixture was filtered with the aid of Celite and the filtrate was concentrated under reduced pressure. The residue was partitioned between dichloromethane and saturated aqueous sodium hydrogencarbonate solution, and the aqueous layer was extracted with dichloromethane. The organic extracts were combined and dried (MgSO$_4$) and the solvent was distilled off under reduced pressure. The residue was chromatographed on silica gel to give the title compound as white amorphous powder (7.9 g, 83%).

$^1$H-NMR (300 MHz, CDCl$_3$) δ: 1.15–1.31 (6H, m), 1.90 (3H, s), 3.21 (2H, s), 3.65 (2H, s), 3.79 (2H, s), 4.09–4.24 (4H, m), 5.01 (2H, s), 6.67–6.80 (4H, m), 7.12–7.26 (8H, m).

IR (KBr): 1717, 1628, 1493, 1406, 1379 cm$^{-1}$.

Reference Example 14

Ethyl 4-(N-benzyl-N-methylaminomethyl)-2-[N-(2,6-difluorobenzyl)-N-ethoxycarbonylamino]-5-[4-(3-methoxyureido)phenyl]thiophene-3-carboxylate

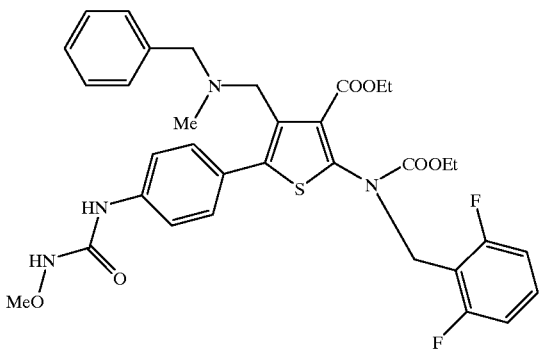

To a solution of the compound obtained in Reference Example 13 (0.9 g, 1.52 mmol) in dichloromethane (20 ml) was added triethylamine (0.43 ml, 3.09 mmol) with ice-cooling. To this solution was added N,N'-carbonyldiimidazole (0.492 g, 3.03 mmol) with ice-cooling, and the mixture was allowed to warm to room temperature and stirred for 48 hours. The reaction mixture was ice-cooled again and O-methylhydroxylamine hydrochloride (1.27 g, 15.2 mmol), triethylamine (2.2 ml, 15.8 mmol) and dichloromethane (5 ml) were added. This reaction mixture was allowed to warm to room temperature and stirred for 3 hours. This reaction mixture was partitioned between chloroform and aqueous sodium hydrogencarbonate solution and the aqueous layer was extracted with chloroform. The organic extracts were combined, washed with aqueous sodium chloride solution and dried (MgSO$_4$), and the solvent was distilled off under reduced pressure. The residue was chromatographed on silica gel to give the title compound as light-yellow amorphous powder (0.93 g, 92%).

¹H-NMR (300 MHz, CDCl₃) δ: 1.16 (3H, br s), 1.29 (3H, t, J=7.1 Hz), 1.91 (3H, s), 3.22 (2H, s), 3.67(2H, s), 3.82(3H, s), 4.17(2H, br s), 4.21(2H, d, J=7.1 Hz), 5.02 (2H, s), 6.78 (2H, t, J=7.8 Hz), 7.12–7.32 (6H, m), 7.40 (2H, d, J=8.6 Hz), 7.53 (2H, d, J=8.6 Hz), 7.62(1H, s).

IR (KBr): 3300, 2982, 1719, 1628, 1591, 1528, 1473, 1408 cm⁻¹.

Reference Example 15

4-(N-Benzyl-N-methylaminomethyl)-2-[N-(2,6-difluorobenzyl)-N-ethoxycarbonylamino]-5-[4-(3-methoxyureido)phenyl]thiophene-3-carboxylic acid

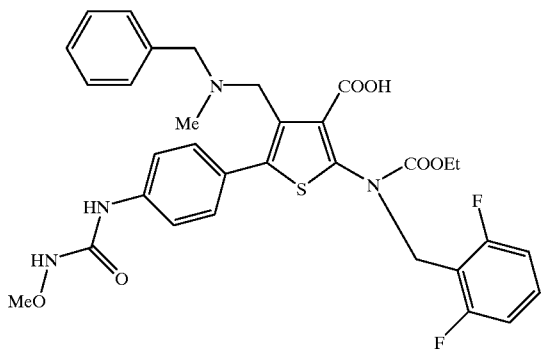

To a solution of the compound obtained in Reference Example 14 (0.1 g, 0.15 mmol) in ethanol (2.5 ml) was added a solution of 2N-sodium hydroxide in water (0.37 ml, 0.74 mmol). This reaction mixture was stirred at room temperature for 1 hour and at 55° C. for a further 18 hours. After cooling, the reaction mixture was neutralized with 2N-hydrochloric acid and partitioned between ethyl acetate and saturated aqueous sodium hydrogencarbonate solution. The aqueous layer was extracted with ethyl acetate. The organic extracts were combined, washed with aqueous sodium chloride solution and dried (MgSO₄) and the solvent was distilled off under reduced pressure. The residue was chromatographed on silica gel to give the title compound as colorless amorphous powder (0.078 g, 81%).

| Elemental analysis for C₃₂H₃₂N₄O₆SF₂ | | | |
|---|---|---|---|
| | C(%) | H(%) | N(%) |
| Calculated: | 60.18; | 5.05; | 8.77 |
| Found: | 60.00; | 5.18; | 8.83 |

¹H-NMR (200 MHz, CDCl₃) δ: 1.0–1.35 (3H, br s), 2.16 (3H, s), 3.84 (3H, s), 3.84 (2H, s), 3.88 (2H, s), 4.10–4.30 (2H, br s), 6.77 (2H, t), 6.70–6.85 (1H, br s), 7.15–7.35 (8H, m), 7.58 (2H, d, J=8.0 Hz), 7.50–7.65 (1H, br s), 7.90–8.00 (1H, br s).

Reference Example 16

4-(N-Benzyl-N-methylaminomethyl)-2-[N-(2,6-difluorobenzyl)-N-ethoxycarbonylamino]-3-(4-methoxymethoxyphenylaminocarbonyl)-5-[4-(3-methoxyureido)phenyl]thiophene

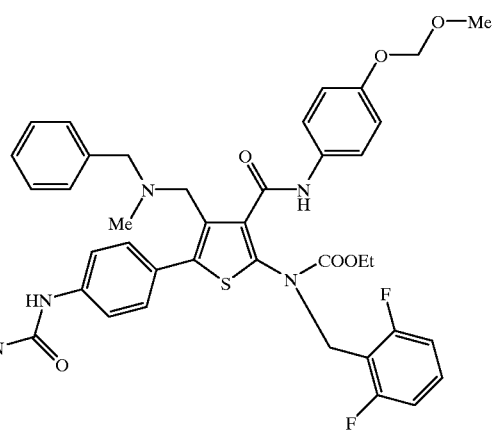

To a solution of the compound obtained in Reference Example 15 (0.80 g, 1.23 mmol), triethylamine (0.88 ml, 6.31 mmol) and 4-methoxymethoxyaniline (0.96 g, 6.27 mmol) in dichloromethane (25 ml) was added benzotriazol-1-yloxytripyrrolidinophosphonium hexafluorophosphate (PyBOP) (0.72 g, 1.38 mmol) with ice-cooling. The mixture was allowed to warm to room temperature and stirred for 14 hours. This reaction mixture was partitioned between chloroform and saturated aqueous sodium hydrogencarbonate solution and the aqueous layer was extracted with chloroform. The organic extracts were combined, washed with aqueous sodium chloride solution and dried (MgSO₄) and the solvent was distilled off under reduced pressure. The residue was chromatographed on silica gel to give the title compound as light-yellow amorphous powder (0.82 g, 93%).

¹H-NMR (300 MHz, CDCl₃) δ: 1.21 (3H, br s), 2.07 (3H, br s), 3.20 (2H, s), 3.47 (3H, s), 3.68 (2H, s), 3.83 (3H, s), 4.24 (2H, br s), 5.07 (2H, br s), 5.13 (2H, s), 6.75 (2H, t, J=7.9 Hz), 6.93 (2H, d, J=9.0 Hz), 7.12–7.18 (3H, m), 7.23–7.25 (4H, m), 7.43 (2H, d, J=9.0 Hz), 7.54 (2H, d, J=8.5 Hz), 7.65 (1H, s).

IR (KBr): 3288, 2940, 1717, 1672, 1628, 1598, 1564, 1528, 1510, 1473 cm⁻¹.

Reference Example 17

Ethyl 2-[N-(2,6-difluorobenzyl)-N-ethoxycarbonylamino]-4-[N-(2-methoxyethyl)-N-methylaminomethyl]-5-(4-nitrophenyl)thiophene-3-carboxylate

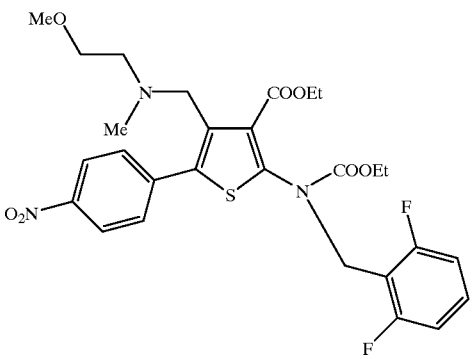

To a solution of the compound obtained in Reference Example 11 (12.82 g, 22.0 mmol) ethyl diisopropylamine (7.7 ml, 44.2 mmol) and N-(2-methoxyethyl)methylamine (3.5 ml, 32.6 mmol) in ethyl acetate (120 ml) was added. The mixture was stirred for 20 hours at room temperature. This reaction mixture was partitioned between ethyl acetate and saturated sodium hydrogencarbonate solution and the aqueous layer was extracted with ethyl acetate. The organic extracts were combined, washed with aqueous sodium chloride solution and dried ($MgSO_4$) and the solvent was distilled off under reduced pressure. The residue was chromatographed on silica gel to give the title compound as a brown oil (10.27 g, 79%).

$^1$H-NMR (300 MHz, $CDCl_3$) [Free amine] δ: 1.16–1.38 (6H, m), 2.08 (3H, s), 2.46 (2H, t, J=6.0 Hz), 3.28 (3H, s), 3.36 (2H, t, J=6.0 Hz), 3.63 (2H, s), 4.09–4.32 (4H, m), 5.01 (2H, s), 6.86 (2H, t, J=8.1 Hz), 7.21–7.32 (1H, m), 7.70 (2H, d, J=8.7 Hz), 8.23 (2H, d, J=8.7 Hz).

IR (KBr): 2984, 1725, 1628, 1597, 1520, 1473 cm$^{-1}$.

FAB-Mass m/z 592(MH)$^+$

Reference Example 18

1-(2,6-Difluorobenzyl)-5-[N-(2-methoxyethyl)-N-methylaminomethyl]-3-(3,4-methylenedioxyphenyl)-6-(4-nitrophenyl)thieno[2,3-d]pyrimidine-2,4(1H,3H)-dione

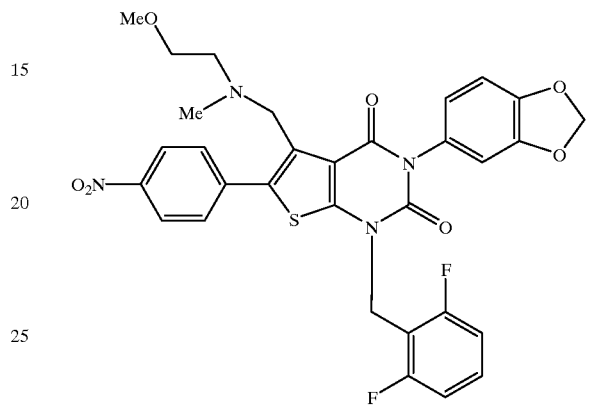

To a solution of 3,4-methylenedioxyaniline (3.30 g, 24.3 mmol) in toluene (80 ml) was added a solution of 1.01 M dimethylaluminium chloride in hexane (22.2 ml, 22.0 mmol) with ice-cooling. This mixture was stirred for 1 hour, with ice-cooling. To this reaction mixture was added a solution of the compound obtained in Reference Example 17 (2.20 g, 3.70 mmol) in toluene (30 ml), and the mixture was stirred for 20 hours at room temperature. This reaction mixture was poured into ice-water, and partitioned between ethyl acetate and saturated sodium hydrogencarbonate solution. The aqueous layer was extracted with ethyl acetate. The organic extracts were combined, washed with aqueous sodium chloride solution and dried ($Na_2SO_4$) and the solvent was distilled off under reduced pressure. The residue was chromatographed on silica gel to give the crude product, which was recrystallized from ethyl acetate-hexane to give the title compound as brown crystals (0.60 g, 68%).

mp: 190–192° C.

| Elemental analysis for $C_{31}H_{26}N_4O_7SF_2$ | | | |
|---|---|---|---|
| | C(%) | H(%) | N(%) |
| Calculated: | 58.49; | 4.12; | 8.80 |
| Found: | 58.50; | 3.91; | 8.61 |

$^1$H-NMR (300 MHz, $CDCl_3$) [Free amine] δ: 2.21 (3H, s), 2.68 (2H, t, J=5.7 Hz), 3.31 (3H, s), 3.44 (2H, t, J=5.7 Hz), 3.87 (2H, s), 5.38 (2H, s), 6.03 (2H, s), 6.73–6.76 (2H, m), 6.90–6.97 (3H, m), 7.28–7.38 (1H, m), 8.00 (2H, d, J=8.7 Hz), 8.26 (2H, d, J=8.7 Hz).

IR (KBr): 2894, 1719, 1671, 1628, 1597, 1547, 1520, 1487, 1462, 1348, 1243 cm$^{-1}$.

Reference Example 19

6-(4-Aminophenyl)-1-(2,6-difluorobenzyl)-5-[N-(2-methoxyethyl)-N-methylaminomethyl]-3-(3,4-methylenedioxyphenyl)thieno[2,3-d]pyrimidine-2,4(1H,3H)-dione

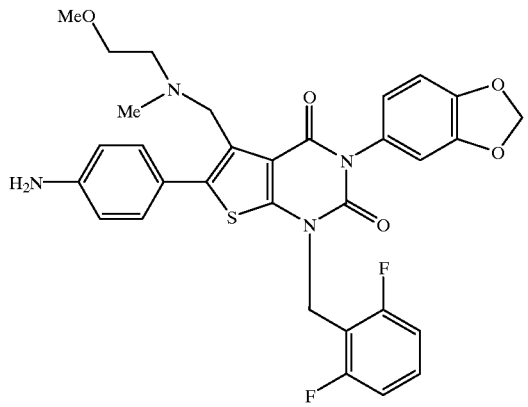

To a solution of the compound obtained in Reference Example 18 (1.56 g, 2.50 mmol) in formic acid (30 ml) were added a solution of 1M hydrogen chloride in ether (7.4 ml, 7.4 mmol) and 10% palladium-on-carbon (200 mg) with ice-cooling, and hydrogenation was carried out under atmospheric conditions at room temperature with constant stirring for 2 hours. This reaction mixture was filtered through Celite and the filtrate was concentrated under reduced pressure. The residue was partitioned between chloroform and saturated aqueous sodium hydrogencarbonate solution. The aqueous layer was extracted with chloroform and the organic extracts were combined, washed with aqueous sodium chloride solution and dried ($Na_2SO_4$). The solvent was then distilled off under reduced pressure. The residue was chromatographed on silica gel to give the crude product, which was recrystallized from ethyl acetate-hexane to give the title compound as brown crystals (1.46 g, 96%).

mp: 200–202° C.

| Elemental analysis for $C_{31}H_{28}N_4O_5SF_2 \cdot 1.0H_2O$ | | | |
|---|---|---|---|
| | C(%) | H(%) | N(%) |
| Calculated: | 59.61; | 4.84; | 8.97 |
| Found: | 59.27; | 4.53; | 8.48 |

$^1$H-NMR (300 MHz, $CDCl_3$) [Free amine] δ: 2.13(3H, s), 2.63 (2H, t, J=5.7 Hz), 3.26 (3H, s), 3.41 (2H, t, J=5.7 Hz), 3.80 (2H, s), 5.34 (2H, s), 6.01 (2H, s), 6.68–6.76 (4H, m), 6.89–6.93 (3H, m), 7.24–7.39 (3H, m).

IR (KBr): 2926, 1715, 1667, 1628, 1533, 1506, 1464 $cm^{-1}$.

Reference Example 20

5-Chloromethyl-1-(2,6-difluorobenzyl)-3-(3,4-ethylenedioxyphenyl)-6-[4-(3-methoxyureido)phenyl]thieno[2,3-d]pyrimidine-2,4(1H,3H)-dione

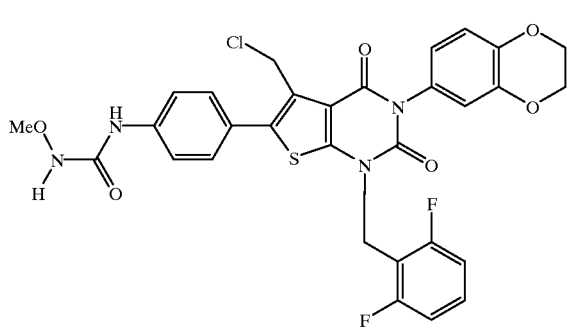

Using the compound obtained in the following Example 8 as a starting material, the title compound was obtained in the same manner as in Reference Example 7.

Yield: 63% mp: 204–209° C.

Example 1

5-(N-Benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione
(Example Compound No. 1)

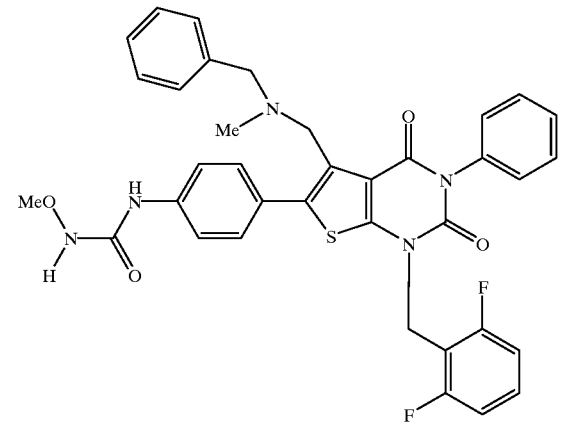

To a solution of the compound obtained in Reference Example 6 (5.0 g, 8.41 mmol) in dichloromethane (120 ml) was added triethylamine (2.34 ml, 16.82 mmol) with ice-cooling, followed by stirring. To this reaction mixture was added N,N'-carbonyldiimidazole (2.73 g, 16.82 mmol) with ice-cooling. The reaction mixture was allowed to warm to room temperature and was stirred for 42 hours. The mixture was then ice-cooled again and O-methylhydroxylamine hydrochloride (7.02 g, 84.08 mmol) and triethylamine (11.7 ml, 84.08 mmol) were added. The reaction mixture was allowed to warm to room temperature and stirred for 3 hours. This reaction mixture was then partitioned between chloroform and saturated sodium hydrogencarbonate solution. The aqueous layer was extracted with chloroform. The extracts were combined, washed with aqueous sodium chloride solution and dried ($MgSO_4$) and the solvent was distilled off under reduced pressure. The residue was chromatographed on silica gel to give the light-yellow solid, which was recrystallized from chloroform-ether to give the title compound as white crystals (4.52 g, 80%).

mp: 204–205° C.

| Elemental analysis for $C_{36}H_{31}N_5O_4SF_2$ | | | |
|---|---|---|---|
| | C(%) | H(%) | N(%) |
| Calculated: | 64.75; | 4.68; | 10.49 |
| Found: | 64.61; | 4.67; | 10.31 |

$^1$H-NMR (300 MHz, CDCl$_3$) δ: 2.05(3H, s), 3.57(2H, s), 3.82(3H, s), 3.90(2H, s), 5.37(2H, s), 6.92(2H, d, J=8.2 Hz), 7.16–7.31(9H, m), 7.42–7.57(5H, m), 7.63(1H, s), 7.73(2H, d, J=8.8 Hz).

IR (KBr): 3338, 3064, 1717, 1669, 1628, 1591, 1531, 1470 cm$^{-1}$.

Example 2

5-(N-Benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione hydrochloride (Example Compound No. 2)

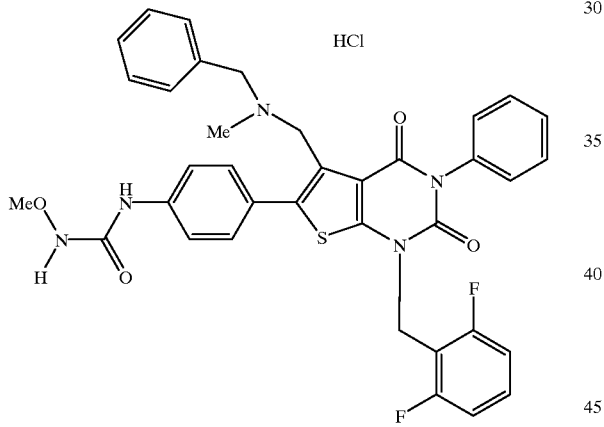

To a solution of the white crystals obtained in Example 1 (38.34 g, 57.42 mmol) in dichloromethane (800 ml) was added hydrogen chloride (1M solution in diethyl ether) (100 ml) with ice-cooling, and the mixture was stirred at the same temperature for 10 minutes. This reaction mixture was concentrated under reduced pressure and the residue was recrystallized from methanol-ether to give the title compound as white powder (40.0 g, 99%).

mp: 182–185° C.

| Elemental analysis for $C_{36}H_{31}N_5O_4SF_2$·HCl·0.5H$_2$O | | | |
|---|---|---|---|
| | C(%) | H(%) | N(%) |
| Calculated: | 60.63; | 4.66; | 9.82 |
| Found: | 60.45; | 4.68; | 9.62 |

IR (KBr): 3440, 3042, 1713, 1665, 1628, 1593, 1539, 1473 cm$^{-1}$.

FAB-Mass m/z 668(MH)$^+$

Example 3

Using the compound obtained in Reference Example 6 as a starting material, Example Compounds No. 3-1 to 3-9 were obtained in the same manner as in Examples 1 and 2.

Example Compound No. 3-1

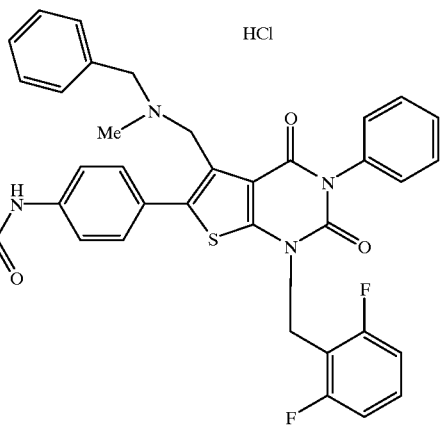

Yield: 91% mp: 175–180° C. [Hydrochloride].

Example Compound No. 3-2

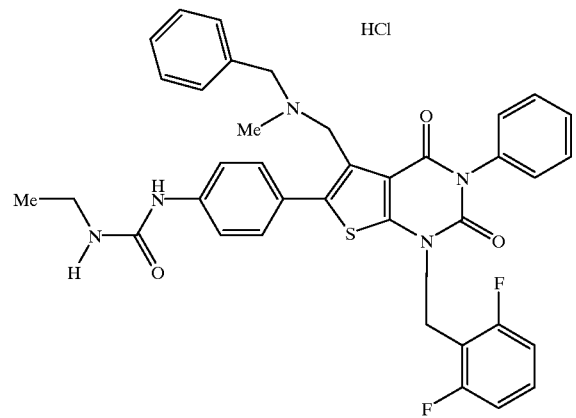

Yield: 81% mp: 179–182° C. [Hydrochloride].

Example Compound No. 3-3
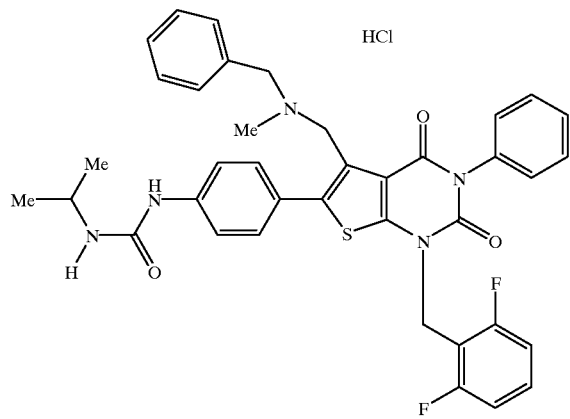
Yield: 80%
mp: 172–177° C. [Hydrochloride].
Example Compound No. 3-4
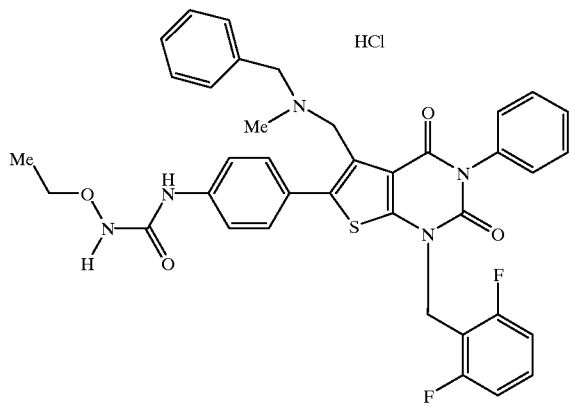
Yield: 99%
mp: 193–197° C. [Hydrochloride].
Example Compound No. 3-5
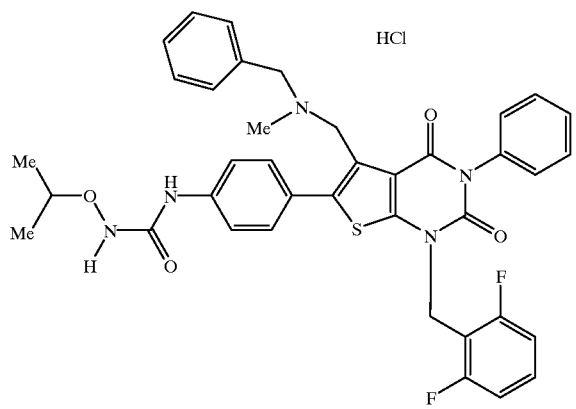
Yield: 91%
mp: 201–204° C. [Hydrochloride].
Example Compound No. 3-6
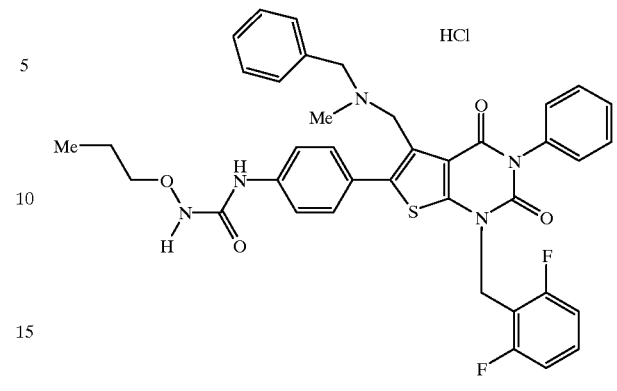
Yield: 89%
mp: 210–215° C. [Hydrochloride].
Example Compound No. 3-7
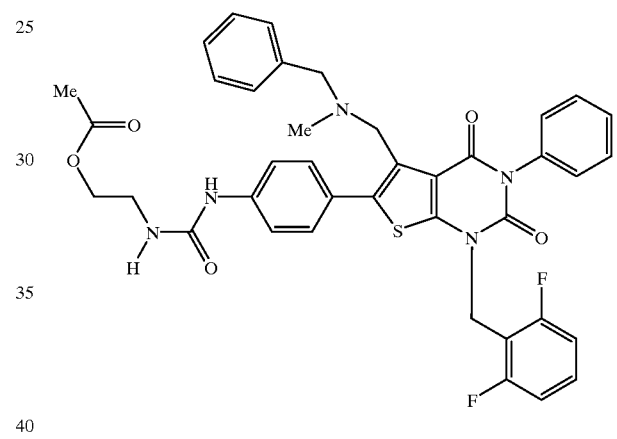
Yield: 89%
mp: 199–200° C. [Free amine].
Example Compound No. 3-8
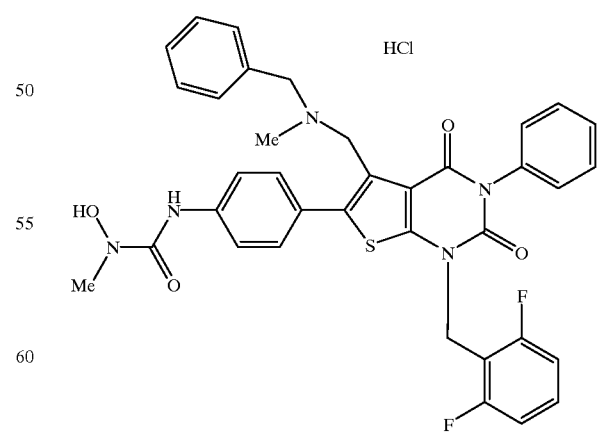
Yield: 93%
mp: 195–198° C. [Hydrochloride].

Example Compound No. 3-9

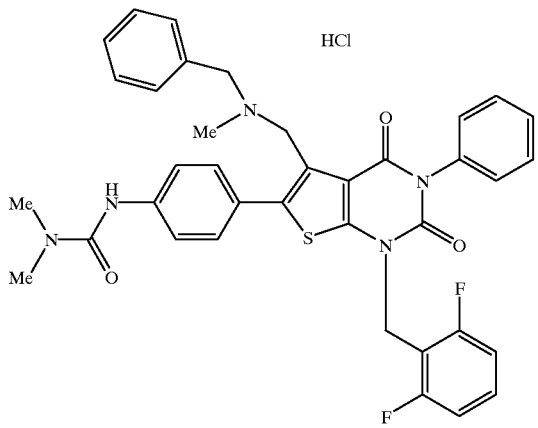

Yield: 95% mp: 165–170° C. [Hydrochloride].

Example 4

Using the compound obtained in Reference Example 7 as a starting material, Example Compounds No. 4-1 to 4-5 were obtained in the same manner as in Reference Example 5.

Example Compound No. 4-1

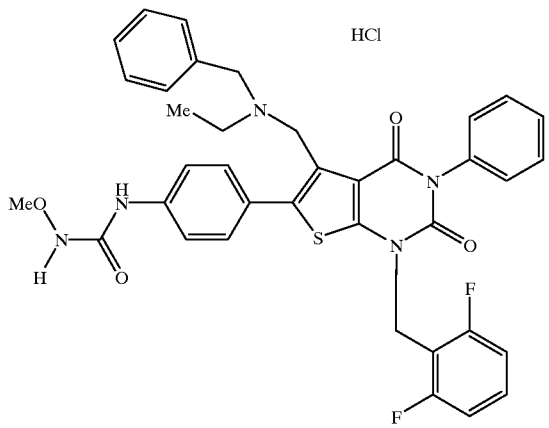

Yield: 80% mp: 177–180° C. [Hydrochloride].

Example Compound No. 4-2

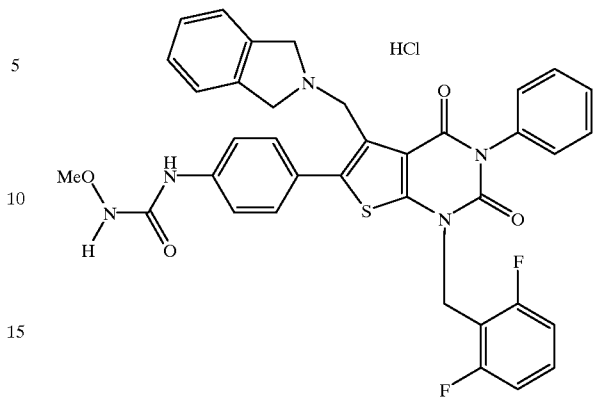

Yield: 77%
mp: 205–210° C. [Hydrochloride].

Example Compound No. 4-3

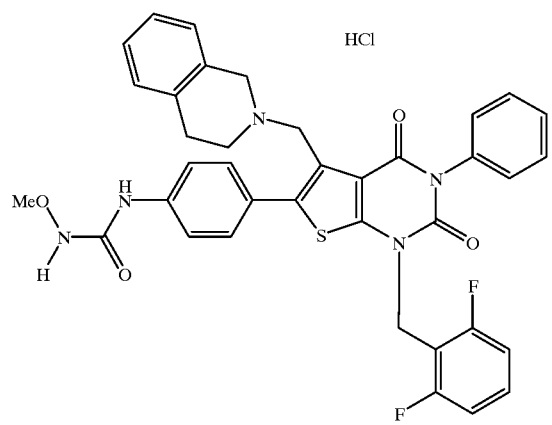

Yield: 77%
mp: 182–185° C. [Hydrochloride].

Example Compound No. 4-4

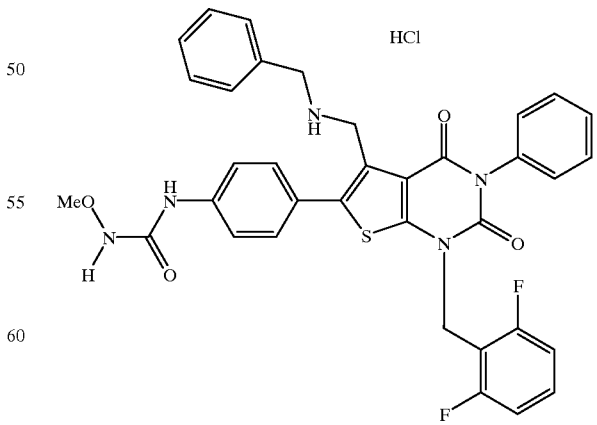

Yield: 14%
mp: 270° C. (dec) [Hydrochloride].

Example Compound No. 4-5

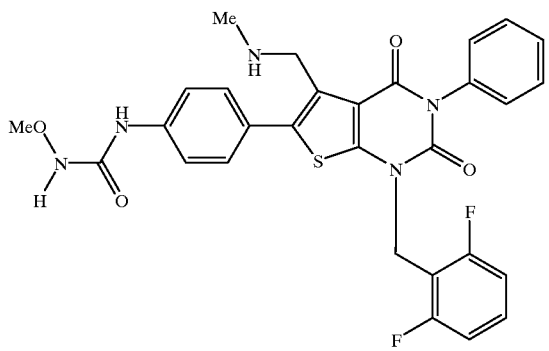

Yield: 26%
mp: 260° C. (dec) [Free amine].

Example 5

5-(N-Benzyl-N-methylaminomethyl)-1-(2,6-difluorobenzyl)-6-[4-(3-hydroxyureido)phenyl]-3-phenylthieno[2,3-d]pyrimidine-2,4(1H,3H)-dione

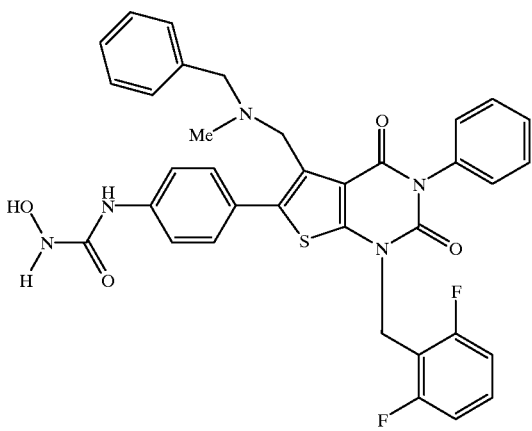

To a solution of the compound obtained in Reference Example 6 (2.0 g, 3.36 mmol) in dichloromethane (40 ml) was added triethylamine (0.94 ml, 6.73 mmol) with ice-cooling, followed by stirring. Then, N,N'-carbonyldiimidazole (1.09 g, 6.73 mmol) was added to the reaction mixture with ice-cooling. The reaction mixture was allowed to warm to room temperature and was stirred for 24 hours. The reaction mixture was ice-cooled again and O-(2,4-dimethoxybenzyl)hydroxylamine (3.11 g, 16.98mmol) was added. The reaction mixture was then allowed to return to room temperature and stirred for 19 hours. This reaction mixture was partitioned between chloroform and saturated aqueous sodium hydrogencarbonate solution and the aqueous layer was extracted with chloroform. The extracts were combined, washed with aqueous sodium chloride solution and dried (MgSO$_4$) and the solvent was distilled off under reduced pressure. To a solution of the residue in dichloromethane (50 ml) was added trifluoroacetic acid (5 ml), followed by stirring at room temperature for 20 minutes. This reaction mixture was partitioned between chloroform and saturated aqueous sodium hydrogencarbonate solution, and the aqueous layer was extracted with chloroform. The extracts were combined, washed with aqueous sodium chloride solution and dried (MgSO$_4$) and the solvent was distilled off under reduced pressure. The residue was chromatographed on silica gel to give white amorphous powder, which was recrystallized from chloroform-ether to give the title compound as white crystals (2.2 g, 100%).

mp: 164–165° C.

$^1$H-NMR (300 MHz, CDCl$_3$) δ: 2.05 (3H, s), 3.46 (2H, s), 3.92 (2H, s), 5.35 (2H, s), 6.65(1H, br), 6.90 (2H, t, J=8.0 Hz), 7.28–7.65 (15H, m), 8.04 (1H, s), 9.73 (1H, br).

IR (KBr): 3326, 2856, 1715, 1665, 1628, 1591, 1531, 1468 cm$^{-1}$.

FAB-Mass m/z 654(MH)$^+$

Example 6

5-(N-Benzyl-N-methylaminomethyl)-1-(2,6-difluorobenzyl)-6-[4-(3-hydroxyureido)phenyl]-3-phenylthieno[2,3-d]pyrimidine-2,4(1H,3H)-dione hydrochloride

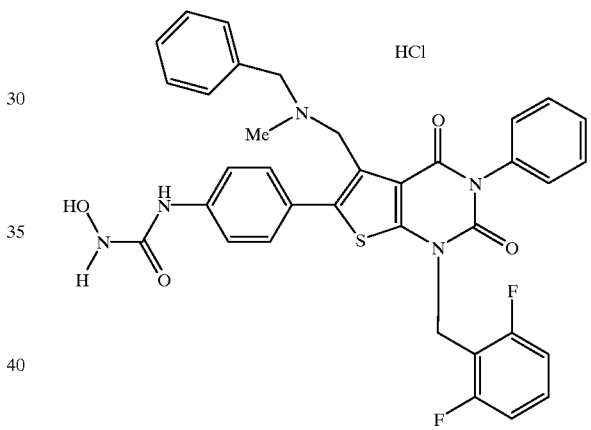

In a solution of the white crystals obtained in Example 5 (60 mg, 0.094 mmol) in dichloromethane (5 ml) was added hydrogen chloride (1M solution in diethyl ether) (0.2 ml) with ice-cooling, followed by stirring at the same temperature for 10 minutes. This reaction mixture was concentrated under reduced pressure and the residue was recrystallized from methanol-ether to give the title compound as white powder (72 mg, 100%).

mp: 180–186° C.

| Elemental analysis for C$_{35}$H$_{29}$N$_5$O$_4$SF$_2$.0.1HCl.1.0H$_2$O | | | |
|---|---|---|---|
| | C(%) | H(%) | N(%) |
| Calculated: | 59.36; | 4.55; | 9.89 |
| Found: | 59.37; | 4.60; | 9.87 |

IR (KBr): 3388, 3066, 1713, 1663, 1628, 1593, 1537, 1473 cm$^{-1}$.

Example 7

5-(N-Benzyl-N-methylaminomethyl)-1-(2,6-difluorobenzyl)-6-[4-[3-(2-hydroxyethyl)ureido]phenyl]-3-phenylthieno[2,3-d]pyrimidine-2,4(1H,3H)-dione

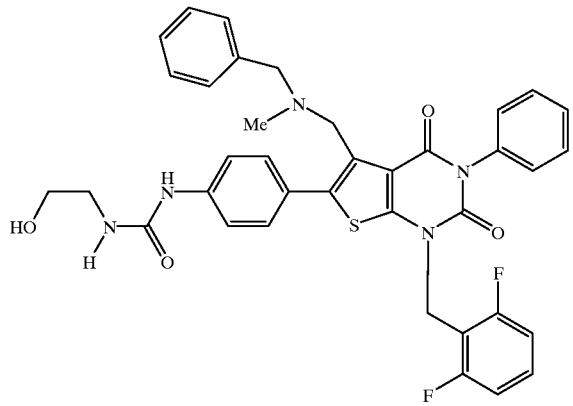

To a solution of the Example Compound No. 3-7 (900 mg, 1.24 mmol) in THF (20 ml) was added 5N-potassium hydroxide solution in water (7 ml) with ice-cooling, followed by stirring at 60° C. for 1 hour. This reaction mixture was partitioned between ethyl acetate and saturated sodium chloride solution and the aqueous layer was extracted with ethyl acetate. The extracts were combined, washed with aqueous sodium chloride solution and dried (MgSO$_4$) and the solvent was distilled off under reduced pressure. The residue was chromatographed on silica gel to give the white amorphous powder, which was recrystallized from chloroform-methanol-ether to give the title compound as white crystals (850 mg, 88%).

mp: 220–222° C.

Elemental analysis for $C_{37}H_{33}N_5O_4SF_2$

| Elemental analysis for $C_{37}H_{33}N_5O_4SF_2$ | | | |
|---|---|---|---|
| | C(%) | H(%) | N(%) |
| Calculated: | 65.18; | 4.88; | 10.27 |
| Found: | 65.08; | 5.01; | 10.29 |

$^1$H-NMR (300 MHz, DMSO-d$_6$) 67 : 1.93 (3H, s), 3.17 (2H, q, J=4.8 Hz), 3.45–3.47 (4H, m), 3.81 (2H, s), 4.76 (1H, t, J=5.1 Hz), 5.28 (2H, s), 6.28(1H, t, J=5.4 Hz), 7.12–7.28 (9H, m), 7.44–7.58 (8H, m), 8.79 (1H, s).

IR (KBr): 3530, 3364, 3066, 2958, 2884, 1715, 1667, 1595, 1531, 1470 cm$^{-1}$.

FAB-Mass m/z 682(MH)$^+$

Example 8

5-(N-Benzyl-N-methylaminomethyl)-1-(2,6-difluorobenzyl)-3-(3,4-ethylenedioxyphenyl)-6-[4-(3-methoxyureido)phenyl]thieno[2,3-d]pyrimidine-2,4(1H,3H)-dione

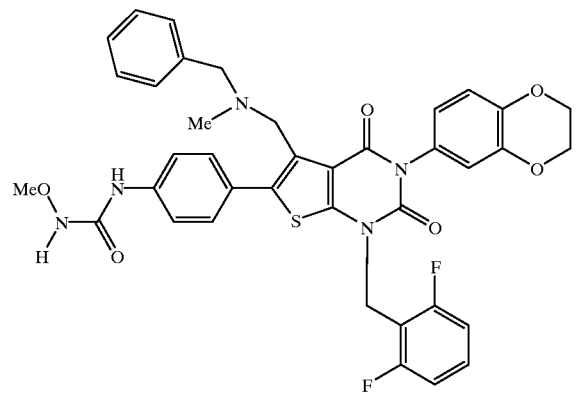

To a solution of 3,4-ethylenedioxyaniline (3.90 g, 25.8 mmol) in dichloromethane (100 ml) was added a solution of 1.01M dimethylaluminum chloride in hexane (25.5 ml, 25.8 mmol) under ice-cooling. The mixture was allowed to warm to room temperature with stirring for 1 hour. To this solution was added a solution of the compound obtained in Reference Example 14 (3.44 g, 5.16 mmol) in dichloromethane (60 ml), and the mixture was stirred at room temperature for 1 day. This reaction mixture was partitioned between chloroform and saturated aqueous sodium chloride solution and the aqueous layer was extracted with chloroform. The organic layers were combined, washed with aqueous sodium chloride solution and dried (MgSO$_4$) and the solvent was distilled off under reduced pressure. The residue was chromatographed on silica gel to give the title compound as white amorphous powder (3.2 g, 85%).

mp: 185–187° C.

| Elemental analysis for $C_{38}H_{34}N_5O_6SF_2Cl.H_2O$ | | | |
|---|---|---|---|
| | C(%) | H(%) | N(%) |
| Calculated: | 58.50; | 4.65; | 8.98 |
| Found: | 58.73; | 4.48; | 9.07 |

$^1$H-NMR (300 MHz, CDCl$_3$) δ: 2.05 (3H, s), 3.57 (2H, s), 3.83 (3H, s), 3.90 (2H, s), 4.29 (4H, s), 5.35 (2H, s), 6.75–7.01 (5H, m), 7.12–7.33 (7H, m), 7.55 (2H, d, J=8.0 Hz), 7.63 (1H, s), 7.72 (2H, d, J=8.0 Hz).

IR (KBr): 1717, 1702, 1686, 1657, 1636, 1626, 1560, 1543, 1522, 1510, 1475 cm$^{-1}$.

Example 9

Using the compound obtained in Reference Example 14 as a starting material, Example Compounds No. 9-1 to 9-2 were obtained in the same manner as in Example 8.

Example Compound No. 9-1

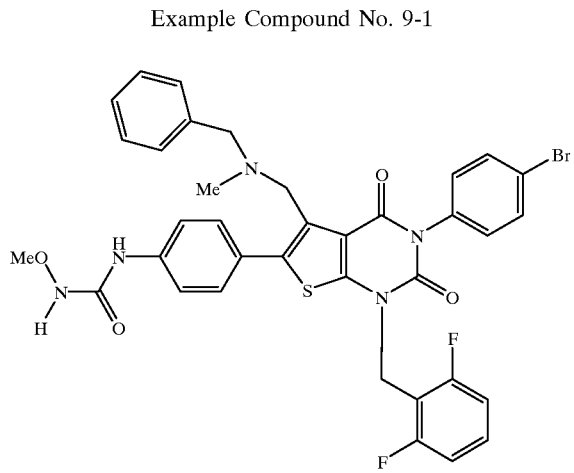

Yield: 60% mp: 148–151° C. [Free amine].

Example Compound No. 9-2

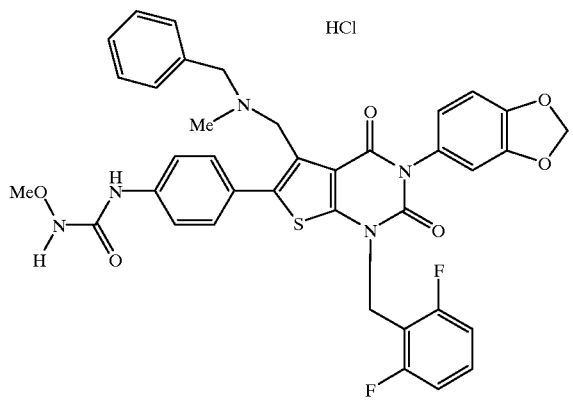

Yield: 54% mp: 169–170° C. [Hydrochloride].

Example 10

5-(N-Benzyl-N-methylaminomethyl)-1-(2,6-difluorobenzyl)-3-[4-(methoxymethoxy)phenyl]-6-[4-(3-methoxyureido)phenyl]thieno[2,3-d]pyrimidine-2,4-(1H,3H)-dione (Example Compound No. 10)

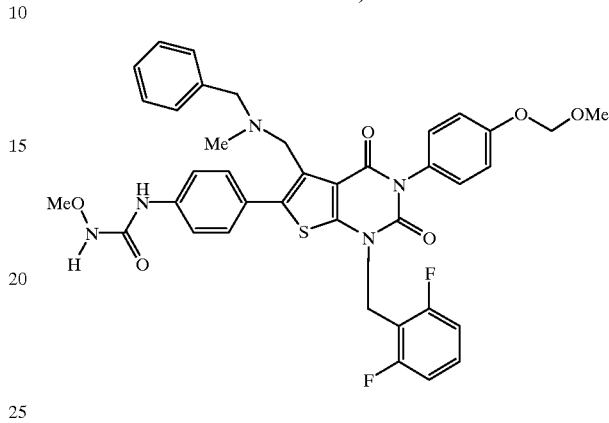

To a solution of the compound obtained in Reference Example 16 (0.84 g, 1.09 mmol) in anhydrous methanol (50 ml) was added a solution of sodium methoxide (2.10 g, 10.4 mmol) in anhydrous methanol (20 ml) with ice-cooling. This mixture was stirred for 2.5 hours, while the temperature was allowed to warm to room temperature. This reaction mixture was neutralized with 1N-hydrochloric acid (10.9 ml, 10.9 mmol) and the solvent was distilled off under reduced pressure. The residue was partitioned between chloroform and saturated aqueous sodium chloride solution and the aqueous layer was extracted with chloroform. The organic extracts were combined, washed with aqueous sodium chloride solution and dried (MgSO$_4$) and the solvent was distilled off under reduced pressure. The residue was recrystallized from ethyl acetate-isopropyl ether to give the title compound as white crystals (0.632 g, 80%).

mp: 189–191° C.

| Elemental analysis for $C_{36}H_{35}N_5O_6SF_2$ | | | |
|---|---|---|---|
|  | C(%) | H(%) | N(%) |
| Calculated: | 62.71; | 4.85; | 9.62 |
| Found: | 62.56; | 4.69; | 9.33 |

$^1$H-NMR (300 MHz, CDCl$_3$) δ: 2.05 (3H, s), 3.49 (3H, s), 3.57 (2H, s), 3.82 (3H, s), 3.91 (2H, s), 5.21 (2H, s), 5.36 (2H, s), 6.92 (2H, d, J=8.0 Hz), 7.14–7.35 (11H, m), 7.55 (2H, d, J=8.5 Hz), 7.63 (1H, s), 7.72 (2H, d, J=8.5 Hz).

IR (KBr): 3380, 2940, 2830, 1717, 1703, 1669, 1628, 1589, 1524, 1464 cm$^{-1}$.

Example 11

5-(N-Benzyl-N-methylaminomethyl)-1-(2,6-difluorobenzyl)-3-(4-hydroxyphenyl)-6-[4-(3-methoxyureido)phenyl]thieno[2,3-d]pyrimidine-2,4-(1H,3H)-dione

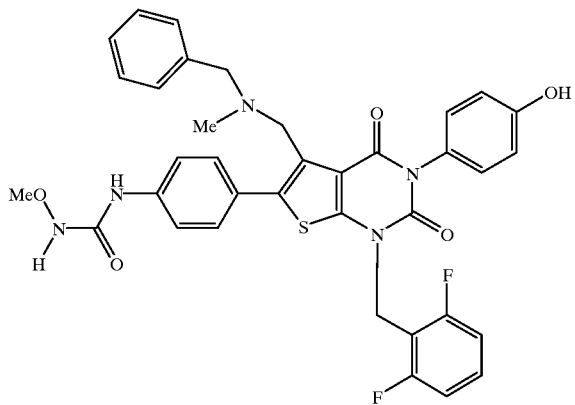

The Example Compound No. 10 (0.35 g, 0.48 mmol) was dissolved in acetone (10 ml), and then was added 6N-hydrochloric acid (1.0 ml, 6.0 mmol). The mixture was stirred at room temperature for 6 hours and neutralized with a solution of 2N-sodium hydroxide (3 ml, 6.0 mmol) in water with ice-cooling and the solvent was distilled off under reduced pressure. The residue was partitioned between chloroform and saturated aqueous sodium chloride solution and the aqueous layer was extracted with chloroform. The organic extracts were combined, washed with aqueous sodium chloride solution and dried ($MgSO_4$) and the solvent was distilled off under reduced pressure. The residue was chromatographed on silica gel to give colorless amorphous powder (0.18 g, 55%), which was recrystallized from chloroform-methanol to give the title compound as white crystals (0.067 g).

mp: 178–182° C.

| Elemental analysis for $C_{36}H_{31}N_5O_5SF_2 \cdot 0.4H_2O$ | | | |
|---|---|---|---|
| | C(%) | H(%) | N(%) |
| Calculated: | 62.58; | 4.64; | 10.14 |
| Found: | 62.78; | 4.57; | 9.86 |

$^1$H-NMR (300 MHz, $CDCl_3$) δ: 2.04 (3H, s), 3.56 (2H, s), 3.80 (3H, s), 3.90 (2H, s), 5.35 (2H, s), 6.89–6.98 (4H, m), 7.08 (2H, d, J=8.8 Hz), 7.15–7.31 (6H, m), 7.57 (2H, d, J=8.6 Hz), 7.69(2H, d, J=8.6 Hz), 7.87(1H, s), 8.27(1H, s), 8.88 (1H, s).

IR (KBr): 3446, 1717, 1663, 1630, 1601, 1534, 1520, 1473 cm$^{-1}$.

Example 12

5-(N-Benzyl-N-methylaminomethyl)-1-(2,6-difluorobenzyl)-6-[4-[(3-methoxy-3-methoxycarbonyl)ureido]phenyl]-3-phenylthieno[2,3-d]pyrimidine-2,4-(1H,3H)-dione

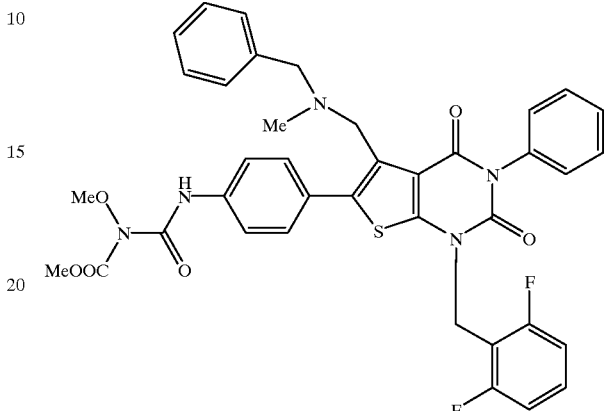

To a solution of the Example Compound No. 1 (0.334 g, 0.5 mmol) in tetrahydrofuran (10 ml) were added triethylamine (0.08 ml, 0.6 mmol) and methyl chloroformate (0.0425 ml, 0.55 mmol) with ice-cooling and the mixture was stirred for 1 hour with ice-cooling and then for 1 hour at room temperature. To this mixture were added triethylamine (0.08 ml, 0.6 mmol) and ethyl chloroformate (0.0425 ml, 0.55 mmol), and the mixture was stirred for 2 hours at 40° C. and then for 2 hours at room temperature. To this mixture was added aqueous sodium chloride solution and extracted with ethyl acetate. The extracts were combined, washed with aqueous sodium chloride solution and dried ($MgSO_4$) and the solvent was distilled off under reduced pressure. The residue was chromatographed on silica gel to give the crude product, which was recrystallized from ethyl acetate-diethyl ether to give the title compound as colorless crystals (0.204 g, 56%).

mp: 150–152° C.

| Elemental analysis for $C_{38}H_{33}N_5O_6SF_2$ | | | |
|---|---|---|---|
| | C(%) | H(%) | N(%) |
| Calculated: | 62.89; | 4.58; | 9.65 |
| Found: | 62.68; | 4.69; | 9.44 |

$^1$H-NMR (200 MHz, $CDCl_3$) δ: 2.06 (3H, s), 3.57 (2H, s), 3.91 (2H, s), 3.93 (3H, s), 3.98 (3H, s), 5.37 (2H, s), 6.92 (2H, t, J=8.2 Hz), 7.15–7.60 (11H, m), 7.57 (2H, d, J=8.6 Hz), 7.73 (2H, d, J=8.6 Hz), 10.06 (1H, s)

IR (KBr): 1746, 1713, 1663, 1537, 1460, 1339, 1200, 1034, 737 cm$^{-1}$.

Example 13

1-(2,6-Difluorobenzyl)-5-[N-(2-methoxyethyl)-N-methylaminomethyl]-6-[4-(3-methoxyureido)phenyl]-3-phenylthieno[2,3-d]pyrimidine-2,4-(1H,3H)-dione

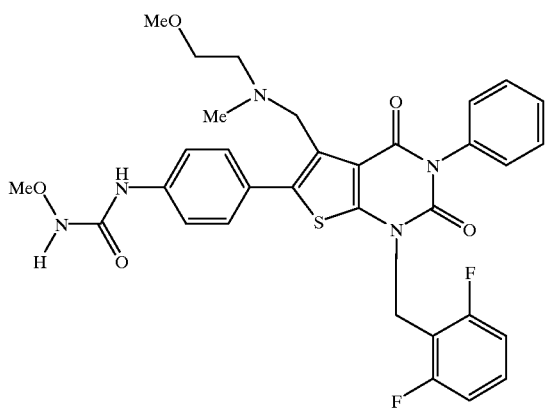

To a solution of the compound obtained in Reference Example 7 (0.86 g, 1.48 mmol) in N,N-dimethylformamide (15 ml) were added ethyldiisopropylamine (0.34 ml, 1.92 mmol), potassium iodide (245 mg, 1.48 mmol) and N-(2-methoxyethyl)methylaime (0.19 ml, 1.78 mmol), and the mixture was stirred at room temperature for 2 hours. This reaction mixture was concentrated to give the residue, which was partitioned between ethyl acetate and saturated aqueous sodium hydrogencarbonate solution. The aqueous layer was extracted with ethyl acetate. The combined extracts were washed with aqueous sodium chloride solution and dried (MgSO$_4$) and the solvent was distilled off under reduced pressure. The residue was chromatographed on silica gel to give the title compound as white crystals (840 mg, 89%).

mp: 161–163° C.

| Elemental analysis for $C_{32}H_{31}N_5O_5SF_2 \cdot 0.5H_2O$ | | | |
|---|---|---|---|
| | C(%) | H(%) | N(%) |
| Calculated: | 59.62; | 5.00; | 10.86 |
| Found: | 59.73; | 4.99; | 10.85 |

$^1$H-NMR (300 MHz, CDCl$_3$) [Free amine] δ: 2.14 (3H, s), 2.64 (2H, t, J=5.9 Hz), 3.27 (3H, s), 3.41 (2H, t, J=5.9 Hz), 3.83 (5H, s), 5.37 (2H, s), 6.93 (2H, t, J=8.2 Hz), 7.12–7.63 (12H, m).

IR (KBr): 1709, 1663, 1560, 1522 cm$^{-1}$.

Example 14

1-(2,6-Difluorobenzyl)-3-(3,4-ethylenedioxyphenyl)-5-[N-(2-methoxyethyl)-N-methylaminomethyl]-6-[4-(3-methoxyureido)phenyl]thieno[2,3-d]pyrimidine-2,4-(1H,3H)-dione

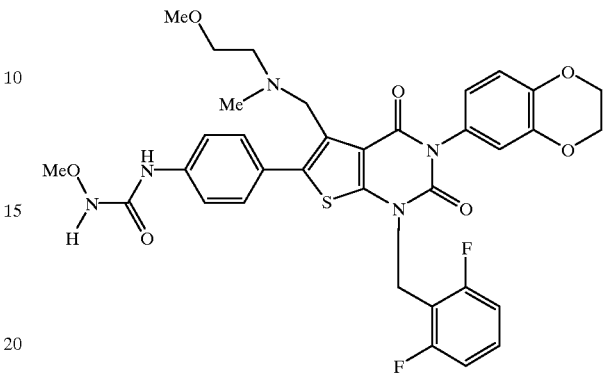

Using the compounds obtained in Reference Example 20 as starting material, the title compound was obtained in the same manner as in Example 13.

Yield: 79% mp: 155–156° C. [Free amine].

Example 15

1-(2,6-Difluorobenzyl)-5-[N-(2-methoxyethyl)-N-methylaminomethyl]-6-[4-(3-methoxyureido)phenyl]-3-(3,4-methylenedioxyphenyl)thieno[2,3-d]pyrimidine-2,4-(1H,3H)-dione

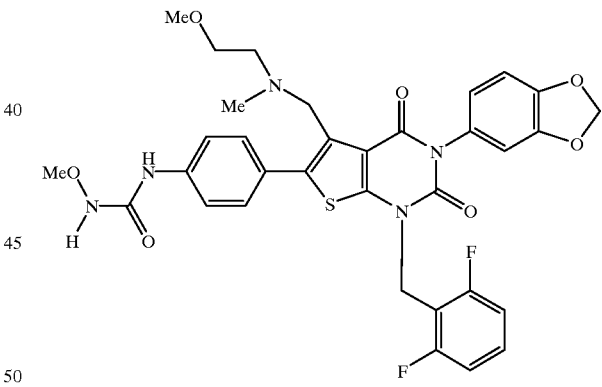

Using the compound obtained in Reference Example 19 as a starting material, the title compound was obtained in the same manner as in Example 1.

Yield: 72% mp: 150–152° C. [Free amine].

Preparation Example 1

Using 100 mg of the Example Compound No. 1, 165 mg of lactose, 25 mg of corn starch, 4 mg of polyvinyl alcohol and 1 mg of magnesium stearate, tablets are produced by a conventional method.

Preparation Example 2

The Example Compound No. 2 (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 3

Using 100 mg of the Example Compound No. 4-2, 165 mg of lactose, 25 mg of corn starch, 4 mg of polyvinyl alcohol and 1 mg of magnesium stearate, tablets are produced by a conventional method.

Preparation Example 4

The Example Compound No. 4-2 (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 5

| (1) | Example Compound No. 1 or No. 4-2 | 5 g |
|---|---|---|
| (2) | Lactose/crystalline cellulose (particles) | 330 g |
| (3) | D-mannitol | 29 g |
| (4) | Low-substitutional hydroxypropyl cellulose | 20 g |
| (5) | Talc | 25 g |
| (6) | Hydroxypropyl cellulose | 50 g |
| (7) | Aspartame | 3 g |
| (8) | Dipotassium glycyrrhizinate | 3 g |
| (9) | Hydroxypropylmethyl cellulose 2910 | 30 g |
| (10) | Titanium oxide | 3.5 g |
| (11) | Yellow iron sesquioxide | 0.5 g |
| (12) | Light silicic anhydride | 1 g |

Components (1), (3), (4), (5), (6), (7) and (8) are suspended or dissolved in purified water and coated on the core particles (2) to yield base fine subtilae, which are then further coated with components (9) through (11) to yield coated fine subtilae, which are then mixed with component (12) to yield 500 g of 1% fine subtilae of the compound. These subtilae are divided to 500 mg folded subtilae.

Experimental Example 1

(1) Preparation of $^{125}$I-leuprorelin

To a tube containing 10 μl of a $3\times10^{-4}$M aqueous solution of leuprorelin and 10 μl of 0.01 mg/ml lactoperoxidase, 10 μl (37MBq) of a solution of Na$^{125}$I was added. After stirring, 10 μl of 0.001% H$_2$O$_2$ was added, and a reaction was carried out at room temperature for 20 minutes. By adding 700 μl of a 0.05% TFA (trifluoroacetic acid) solution, the reaction was stopped, followed by purification by reversed-phase HPLC. The HPLC conditions used are shown below. $^{125}$I-leuprorelin was eluted at a retention time of 26 to 27 minutes. Column: TSKgel ODS-80™ (TM indicates a registered trademark; the same applies below) CTR (4.6 mm×10 cm)
Eluents:

Solvent A (0.05% TFA)

Solvent B (40% CH$_3$CN-0.05% TFA)

0 minute (100% Solvent A)–3 minutes (100% Solvent A)–7 minutes (50% Solvent A+50% Solvent B)–40 minutes (100% Solvent B)

Eluting temperature: Room temperature
Elution rate: 1 ml/min (2) Preparation of a Rat Pituitary Anterior Lobe Membrane Fraction Containing GnRH Receptors Anterior lobes of the pituitary glands were isolated from forty Wistar rats (8 weeks old, male), and washed with ice-cooled homogenate buffer [25 mM Tris (tris (hydroxymethyl)aminomethane)-HCl, 0.3 M sucrose, 1 mM EGTA (glycol-etherdiamine-N,N,N',N'-tetraacetic acid), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide, pH 7.5]. The pituitary tissue was floated in 2 ml of the homogenate buffer and homogenized using a Polytron homogenizer. The homogenate was centrifuged at 700×g for 15 minutes. The supernatant was taken in an ultracentrifuge tube and centrifuged at 100,000×g for 1 hour to give a membrane fraction pellet. This pellet was suspended in 2 ml of assay buffer [25 mM Tris-HCl, 1 mM EDTA (ethylenediaminetetraacetic acid), 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5] and the suspension was centrifuged at 100,000×g for 1 hour. The membrane fraction recovered as a pellet was resuspended in 10 ml of assay buffer, divided into portions, preserved at −80° C. and thawed when needed.

(3) Preparation of CHO (Chinese Hamster Ovarian) Cell Membrane Fraction Containing Human GnRH Receptor Human GnRH receptor-expressing CHO cells ($10^9$ cells) were suspended in phosphate-buffered saline supplemented with 5 mM EDTA (ethylenediaminetetraacetic acid) (PBS-EDTA) and centrifuged at 100×g for 5 minutes. To the cell pellet, 10 ml of a cell homogenate buffer (10 mM NaHCO$_3$, 5 mM EDTA, pH 7.5) was added, followed by homogenization using the Polytron homogenizer. After centrifugation at 400×g for 15 minutes, the supernatant was transferred to an ultracentrifugation tube and centrifuged at 100,000×g for 1 hour to yield a membrane fraction precipitate. This precipitate was suspended in 2 ml of an assay buffer and centrifuged at 100,000×g for 1 hour. The membrane fraction recovered as a precipitate was again suspended in 20 ml of the assay buffer, dispensed, and stored at −80° C. before use upon thawing.

(4) Determination of $^{125}$I-leuprorelin Binding Inhibition Rate

The rat and human membrane fractions prepared in the above (2) and (3) were diluted with the assay buffer to yield a 200 μg/ml dilution, which was then dispensed at 188 μl per tube. Where the rat pituitary anterior lobe membrane fraction was used, to each tube, 2 μl of a solution of 0.1 mM compound in 60% DMSO (dimethyl sulfoxide) and 10 μl of 38 nM $^{125}$I-leuprorelin were added simultaneously. Where the cell membrane fraction of the CHO with human GnRH receptors expressed, to each tube, 2 μl of a solution of 2 mM compound in 60% DMSO and 10 μl of 38 nM $^{125}$I-leuprorelin were added simultaneously. To determine maximum binding quantity, a reaction mixture of 2 μl of 60% DMSO and 10 μl of 38 nM $^{125}$I-leuprorelin was prepared. To determine non-specific binding amount, a reaction mixture of 2 μl of 100 μM leuprorelin in solution in 60% DMSO and 10 μl of 38 nM $^{125}$I-leuprorelin was prepared.

Where the rat pituitary anterior lobe membrane fraction was used, the reaction was conducted at 4° C. for 90 minutes. Where the membrane fraction of the CHO with human GnRH receptors expressed was used, the reaction was carried out at 25° C. for 60 minutes. After each reaction, the reaction mixture was aspirated and filtered through a polyethyleneimine-treated Whatman glass filter (GF-F).

After this filtration, the radioactivity of $^{125}$I-leuprorelin remaining on the filter paper was measured with a γ-counter.

The expression (TB-SB)/(TB-NSB)×100 (where SB=radioactivity with the compound added, TB=maximum bound radioactivity, NSB=nonspecifically bound radioactivity) was calculated to find the binding inhibition rate (%) of each test compound. Furthermore, the inhibition rate was determined by varying the concentration of the test substance and the 50% inhibitory concentration (IC$_{50}$ value) of the compound was calculated from Hill plot. The results are shown in below.

| Test Compound | binding inhibition rate (%) | | IC$_{50}$ value (μM) | |
|---|---|---|---|---|
| | Rat (1 μM) | Human (20 μM) | Rat | Human |
| Ex. Compd. No. 2 | 27 | NT | NT | 0.0001 |
| Ex. Compd. No. 4-2 | 64 | NT | 0.5 | 0.0002 |

NT: not measured

Experimental Example 2

Suppression of Plasma LH in Castrated Monkeys

The Example compound No. 2 was orally administered to castrated male cynomolgus monkeys (Macaca fascicularis), and plasma LH was quantified. The male cynomolgus monkeys, used at 4 years 9 months to 6 years 3 months of age at time of experimentation, had been castrated more than 3 months prior to the examination. Test animals [n=3] were given 30 mg/kg (3 ml/kg) of the compound suspended in 0.5% methyl cellulose at a final concentration of 1% by oral administration, and control animals [n=2] were given 3 ml/kg of the 0.5% methyl cellulose dispersant alone by oral administration. At 24 hours and immediately before administration and at 2, 4, 6, 8, 24, and 48 hours after administration, blood was collected for heparinized plasma samples via the femoral vein and immediately stored under freezing conditions.

Plasma LH concentrations were determined by a bioassay using mouse testicular cells. The testicular cells were collected from male BALB/c mice (8 to 9 weeks of age) and washed three times with 1 ml of Dulbecco's modified Eagle medium. (DMEM-H) containing 20 mM HEPES and 0.2% BSA per testis. After incubation at 37° C. for 1 hour, the cells were passed through a nylon mesh filter (70 μm) and dispensed to test tubes at 8×10$^5$ cells/tube. After the cells were washed twice with 0.4 ml of DMEM-H, 0.4 ml of a DMEM-H solution containing either equine LH (Sigma Company), as the standard LH, or monkey plasma, previously diluted up to 300 fold, as the test sample, was added, followed by a reaction at 37° C. for 2 hours. The testosterone concentration in the culture supernatant was determined by a radioimmunoassay (CIS Diagnostics Company), and the LH concentration in the test monkey plasma was calculated from the standard curve for the standard equine LH.

The results are given together in FIG. 1.

The LH concentration is expressed in the percentage (%) of the baseline LH concentration immediately before administration in each individual cynomolgus monkey and is shown as the time course with the administration time being taken as 0 (indicated by the arrowmark) and values before and after administration being indicated by the minus and plus signs, respectively. The control group-1 (-▲-) and control group-2 (-♦-) were orally dosed with 0.5% methyl-cellulose dispersant (3 ml/kg) only, while the compound group-1 (-△-), compound group-2 (-□-) and compound group-3 (-○-) similarly received a dispersion of the Example Compound No. 2 in 0.5% methylcellulose (30 mg/kg, 3 ml/kg).

The control groups showed little change in the plasma LH concentration even after administration. On the other hand, in the compound groups, the plasma LH concentration showed a rapid fall beginning immediately after administration and had fallen to 20% of the baseline or less by 24 hours after administration. Then, at 48 hours after administration, re-elevation of the plasma LH concentration was noted.

The above results indicate that the Example Compound No. 2, administered orally, has a significant depressive effect on blood LH concentration.

It is evident from the foregoing results that compounds of the present invention antagonize the pituitary LH-RH receptors to block the LH-RH stimulation from the hypothalamus to inhibit the LH release.

INDUSTRIAL APPLICABILITY

A compound of the present invention possesses excellent gonadotropin-releasing hormone antagonizing activity. It is also good in oral absorbability and excellent in stability and pharmacokinetics. With low toxicity, it is also excellent in safety. Therefore, the compound of the present invention can be used as a prophylactic or therapeutic agent for hormone-dependent diseases etc. Concretely, it is effective as a prophylactic or therapeutic agent for sex hormone-dependent cancers (e.g., prostatic cancer, uterine cancer, breast cancer, pituitary tumor, etc.), prostatic hypertrophy, hysteromyoma, endometriosis, precocious puberty, amenorrhea syndrome, multilocular ovary syndrome, pimples etc, or as a pregnancy regulator (e.g., contraceptive), infertility remedy or menstruation regulator. It is also effective as an animal estrous regulator, food meat quality improving agent or animal growth regulator in the field of animal husbandry, and as a fish spawning promoter in the field of fishery.

What is claimed is:

1. A compound of the formula:

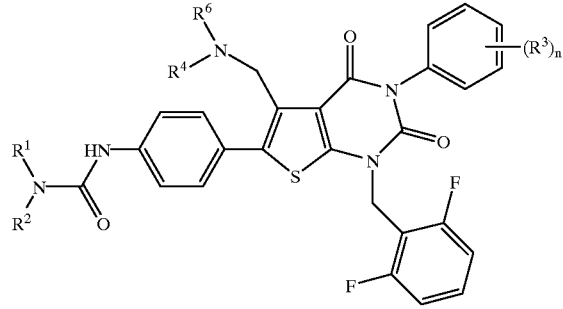

wherein $R^1$ and $R^2$ each represents a hydrogen atom, a hydroxy group, a $C_{1-4}$ alkoxy group, a $C_{1-4}$ alkoxy-carbonyl group or a $C_{1-4}$ alkyl group which may be substituted by 1 to 5 substituents selected from the group consisting of (i) hydroxy, (ii) $C_{1-7}$ acyloxy, (iii) benzoyloxy, (iv) amino which may be substituted by 1 or 2 substituents selected from the group consisting of $C_{1-6}$ alkoxy-carbonyl, benzyloxycarbonyl, $C_{1-4}$ acyl, $C_{1-4}$ alkyl and $C_{1-3}$ alkylsulfonyl, (v) $C_{1-10}$ alkoxy, (vi) $C_{3-7}$ cycloalkyloxycarbonyl-$C_{1-3}$ alkoxy and (vii) $C_{1-3}$ alkoxy-$C_{1-3}$ alkoxy;

R³ represents a hydrogen atom, a halogen atom, a hydroxy group or a C₁₋₄ alkoxy group which may be substituted by 1 to 5 substituents selected from the group consisting of (i) hydroxy, (ii) C₁₋₇ acyloxy, (iii) benzoyloxy, (iv) amino which may be substituted by 1 or 2 substituents selected from the group consisting of C₁₋₆ alkoxy-carbonyl, benzyloxycarbonyl, C₁₋₄ acyl, C₁₋₄ alkyl and C₁₋₃ alkylsulfonyl, (v) C₁₋₁₀ alkoxy, (vi) C₃₋₇ cycloalkyloxycarbonyl-C₁₋₃ alkoxy and (vii) C₁₋₃ alkoxy-C₁₋₃ alkoxy; or two adjacent R³ may form, taken together, a C₁₋₄ alkylenedioxy group;

R⁴ represents a hydrogen atom or a C₁₋₄ alkyl group;

R⁶ represents a C₁₋₄ alkyl group which may be substituted by 1 to 5 substituents selected from the group consisting of (i) hydroxy, (ii) C₁₋₇ acyloxy, (iii) benzoyloxy, (iv) amino which may be substituted by 1 or 2 substituents selected from the group consisting of C₁₋₆ alkoxycarbonyl, benzyloxycarbonyl, C₁₋₄ acyl, C₁₋₄ alkyl and C₁₋₃ alkylsulfonyl, (v) C₁₋₁₀ alkoxy, (vi) C₃₋₇ cycloalkyloxycarbonyl-C₁₋₃ alkoxy and (vii) C₁₋₃ alkoxy-C₁₋₃ alkoxy; or a group of the formula:

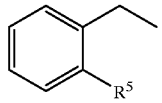

wherein R⁵ represents a hydrogen atom, or R⁴ and R⁵ may together form

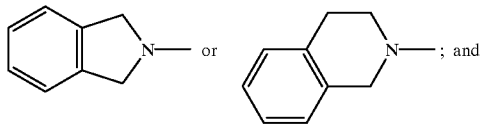

; and n represents an integer of 0 to 5, or a salt thereof.

2. A compound of claim 1 or a salt thereof, which is a compound of the formula:

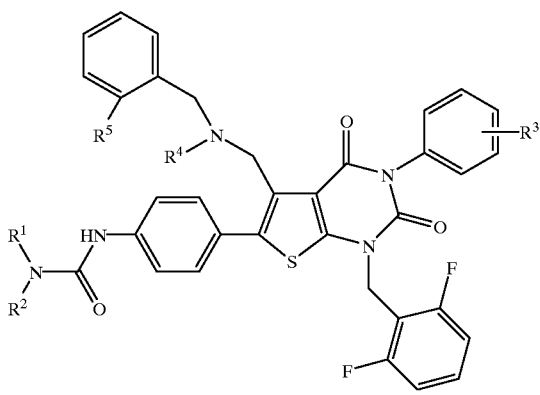

wherein R¹ and R² each is a hydrogen atom, a hydroxy group, a C₁₋₄ alkoxy group or a C₁₋₄ alkyl group which may be substituted by 1 to 5 substituents selected from the group consisting of (i) hydroxy, (ii) C₁₋₇ acyloxy, (iii) benzoyloxy, (iv) amino which may be substituted by 1 or 2 substituents selected from the group consisting of C₁₋₆ alkoxy-carbonyl, benzyloxycarbonyl, C₁₋₄ acyl, C₁₋₄ alkyl and C₁₋₃ alkylsulfonyl, (v) C₁₋₁₀ alkoxy, (vi) C₃₋₇ cycloalkyloxycarbonyl-C₁₋₃ alkoxy and (vii) C₁₋₃ alkoxy-C₁₋₃ alkoxy;

R³ is a hydrogen atom, a halogen atom or a C₁₋₄ alkoxy group which may be substituted by 1 to 5 substituents selected from the group consisting of (i) hydroxy, (ii) C₁₋₇ acyloxy, (iii) benzoyloxy, (iv) amino which may be substituted by 1 or 2 substituents selected from the group consisting of C₁₋₆ alkoxy-carbonyl, benzyloxycarbonyl, C₁₋₄ acyl, C₁₋₄ alkyl and C₁₋₃ alkylsulfonyl, (v) C₁₋₁₀ alkoxy, (vi) C₃₋₇ cycloalkyloxycarbonyl-C₁₋₃ alkoxy and (vii) C₁₋₃ alkoxy-C₁₋₃ alkoxy; or two adjacent R³ may form, taken together, a C₁₋₄ alkylenedioxy group;

R⁴ is a C₁₋₄ alkyl group; and

R⁵ is a hydrogen atom, or R⁴ and R⁵ may together form

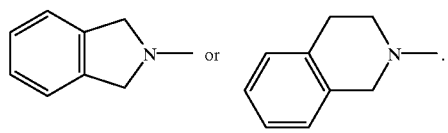

3. A compound of claim 1 or a salt thereof, wherein R¹ is a C₁₋₃ alkoxy group.

4. A compound of claim 3 or a salt thereof, wherein R² is a hydrogen atom.

5. A compound of claim 1 or a salt thereof, wherein R³ is a hydrogen atom.

6. A compound of claim 1 or a salt thereof, wherein R⁶ is a group of the formula:

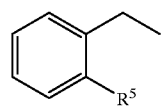

wherein R⁵ is as defined in claim 1.

7. A compound of claim 2 or a salt thereof, wherein R⁴ is a C₁₋₃ alkyl group and R⁵ is a hydrogen atom.

8. A compound of claim 1 or a salt thereof, wherein n is 1 or 2.

9. A compound of claim 1, or a salt thereof, wherein R¹ is (i) a hydroxy group, (ii) a C₁₋₄ alkoxy group, or (iii) a C₁₋₄ alkyl group which may be a substituted by hydroxy or C₁₋₄ alkyl-carbonyloxy;

R² is a hydrogen atom, a C₁₋₄ alkyl group or a C₁₋₄ alkoxy-carbonyl group;

R³ represents a hydrogen atom, a halogen atom, a hydroxy group or a C₁₋₄ alkoxy-C₁₋₄ alkoxy group;

or two adjacent R³ may form, taken together, a C₁₋₄ alkylenedioxy group;

R⁴ is a hydrogen atom or a C₁₋₃ alkyl group;

R⁶ is a C₁₋₄ alkoxy-C₁₋₄ alkyl group or a group of the formula:

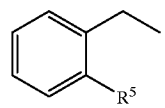

wherein R⁵ is a hydrogen atom, or R⁴ and R⁵ may together form

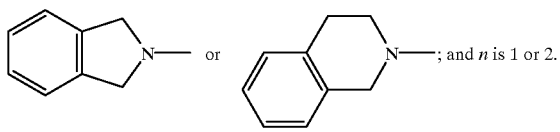 ; and *n* is 1 or 2.

10. A compound of claim 1 or a salt thereof, wherein
$R^1$ is a hydroxy group, a methoxy group or a $C_{1-3}$ alkyl group;
$R^2$ is a hydrogen atom or a $C_{1-3}$ alkyl group;
$R^4$ is a $C_{1-3}$ alkyl group;
$R^6$ is a benzyl group; and
n is 0.

11. A process for producing a compound of claim 1 or a salt thereof, which comprises reacting a compound of the formula:

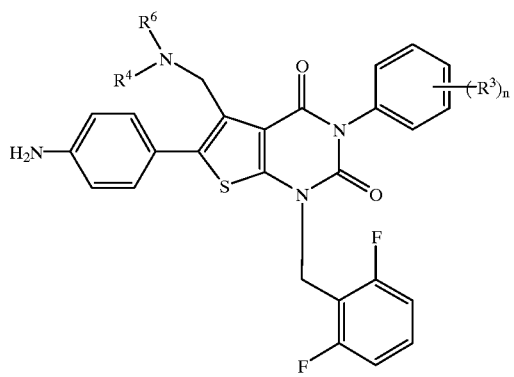

wherein each symbol is as defined in claim 1, or a salt thereof with carbonyldiimidazole or phosgene, followed by reacting with a compound of the formula:

wherein each symbol is as defined in claim 1, or a salt thereof.

12. A pharmaceutical composition which comprises a compound of claim 1 or a salt thereof and a pharmaceutically acceptable carrier, excipient or diluent.

13. 5-(N-Benzyl-N-methylaminomethyl)-1-(2,6-difluorobenzyl)-6-[4-(3-ethylureido)phenyl]-3-phenylthieno[2,3-d]pyrimidine-2,4(1H,3H)-dione or a salt thereof.

14. 5-(N-Benzyl-N-methylaminomethyl)-1-(2,6-difluorobenzyl)-6-[4-(3-ethylureido)phenyl]-3-phenylthieno[2,3-d]pyrimidine-2,4(1H,3H)-dione hydrochloride.

15. A method for treating gonadotropin sensitive cancer by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

16. A method for treating gonadotropin sensitive prostatic hypertrophy by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

17. A method for treating gonadotropin sensitive hysteromyoma by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

18. A method for treating gonadotropin sensitive endometriosis by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

19. A method for treating gonadotropin sensitive precocious puberty by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

20. A method for treating gonadotropin sensitive amenorreha by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

21. A method for treating gonadotropin sensitive premenstrual syndrome by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

22. A method for treating gonadotropin sensitive multiocular ovary syndrome by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

23. A method for treating gonadotropin sensitive pimples by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

24. A method for treating gonadotropin sensitive infertility by antagonizing gonadotropin-releasing hormone in a mammal in need thereof, which comprises administering to said mammal an effective amount of a compound of claim 1 or a salt thereof with a pharmaceutically acceptable excipient, carrier or diluent such that gonadotropin-releasing hormone is antagonized.

* * * * *